US007265227B2

(12) United States Patent
Evans et al.

(10) Patent No.: US 7,265,227 B2
(45) Date of Patent: Sep. 4, 2007

(54) PIPERIDINE DERIVATIVES USEFUL AS MODULATORS OF CHEMOKINE RECEPTOR ACTIVITY

(75) Inventors: Richard Evans, Loughborough (GB); Matthew Perry, Loughborough (GB); Brian Springthorpe, Loughborough (GB)

(73) Assignee: AstraZeneca AB, Södertälje (SE)

( * ) Notice: Subject to any disclaimer, the term of this patent is extended or adjusted under 35 U.S.C. 154(b) by 227 days.

(21) Appl. No.: 10/483,138

(22) PCT Filed: Jul. 19, 2002

(86) PCT No.: PCT/SE02/01401

§ 371 (c)(1),
(2), (4) Date: Jan. 8, 2004

(87) PCT Pub. No.: WO03/018556

PCT Pub. Date: Mar. 6, 2003

(65) Prior Publication Data

US 2004/0176411 A1    Sep. 9, 2004

(30) Foreign Application Priority Data

Jul. 23, 2001   (GB)   ................. 0117899.5

(51) Int. Cl.
*C07D 211/06*    (2006.01)
(52) U.S. Cl. ...................... 546/216; 546/242
(58) Field of Classification Search .......... 546/192, 546/242, 216
See application file for complete search history.

(56) References Cited

U.S. PATENT DOCUMENTS

| | | | |
|---|---|---|---|
| 4,335,127 A | 6/1982 | Vandenberk et al. | |
| 4,853,393 A | 8/1989 | Zimmermann | |
| 5,143,923 A | 9/1992 | Hrib et al. | |
| 5,210,086 A | 5/1993 | George et al. | |
| 6,140,344 A | 10/2000 | Gong et al. | |
| 6,518,286 B1 | 2/2003 | Baxter et al. | 514/327 |
| 2003/0050309 A1 | 3/2003 | Aquila et al. | 514/227.5 |
| 2003/0166652 A1 | 9/2003 | Sanganee et al. | 514/235.5 |
| 2004/0102432 A1 | 5/2004 | Sanganee et al. | 514/210.2 |
| 2004/0209879 A1 | 10/2004 | Gustafsson et al. | 514/235.2 |

FOREIGN PATENT DOCUMENTS

| | | |
|---|---|---|
| EP | 0124476 A1 | 11/1984 |
| EP | 0184258 A2 | 5/1986 |
| EP | 0288563 A1 | 11/1988 |
| EP | 0429341 | 5/1991 |
| EP | 0515240 | 11/1992 |
| EP | 0661266 | 7/1995 |
| EP | 0903349 | 3/1999 |
| FR | 2675801 | 10/1992 |
| FR | 2724382 A1 | 3/1996 |
| GB | 1243991 | 8/1971 |
| GB | WO 01/92227 | * 12/2001 |
| JP | 03264579 | 11/1991 |
| JP | 09040646 | 2/1997 |
| JP | 09077742 | 3/1997 |
| WO | WO96/14317 | 5/1996 |
| WO | WO96/29330 | 9/1996 |
| WO | WO97/10207 | 3/1997 |
| WO | WO97/42956 | 11/1997 |
| WO | WO97/49680 | 12/1997 |
| WO | WO99/04794 | 2/1999 |
| WO | WO99/37617 | 7/1999 |
| WO | WO99/37619 | 7/1999 |
| WO | WO99/38514 | 8/1999 |
| WO | WO 00/29377 | 5/2000 |
| WO | WO 00/35877 | 6/2000 |
| WO | WO 00/58305 | 10/2000 |
| WO | WO 01/14333 | 3/2001 |
| WO | WO 02/20484 | 3/2002 |
| WO | WO 02/30899 | 4/2002 |
| WO | WO 03/018566 | 3/2003 |

OTHER PUBLICATIONS

Cohen et al., Am. J. Clin. Pathol., 1996, 105, 589.*
Bungaard, "Design of Prodrugs", 1985, p. 1.*
U.S. Appl. No. 10/339,261, filed Jul. 17, 2003, Baxter et al.
CAS printout for Vandenberk et al., Chem. Abs. 97:856 (1982).
CAS printout for Kikuchi et al., Chem. Abs. 128:22926 (JP 09291090).
CAS printout for Takahashi et al., Chem Abs. 128:294706 (JP 10077271).
Herndon et al., "Ketanserin Analogues: Structure-Affinity Relationships for 5-HT$_2$ and 5-HT$_{IC}$ Serotonin Receptor Binding," *J. Med. Chem.* 35:4903-4910 (1992).
Hrib et al., "Benzisoxazole- and Benzisothiazole-3-carboxamides as Potential Atypical Antipsychotic Agents," *J. Med. Chem.* 37:2308-2314 (1994).

(Continued)

*Primary Examiner*—Celia Chang
(74) *Attorney, Agent, or Firm*—Fish & Richardson P.C.

(57) ABSTRACT

The invention provides compounds of formula (I) wherein: T is C(O) or S(O)$_2$; W is C(O) or S(O)$_2$; X is CH$_2$, O or NH; Y is CR$_{11}$ or N; n is 0, 1 or 2; m is 1 or, when Y is CR$_{11}$ m is 0; R$_1$ is optionally substituted aryl or optionally substituted heterocyclyl; R$_2$, R$_3$, R$_{.4}$, R$_5$, R$_6$, R$_7$ and R$_8$ are, independently, hydrogen or C?1-6#191 alkyl; R$_9$ is hydrogen or C$_1$-C$_6$ alkyl; R$_{10}$ is alkyl, optionally substituted aryl, optionally substituted aralkyl or optionally substituted heterocyclyl; and R$_{11}$ is hydrogen or C$_1$-C$_6$ allkyl; that are modulators of chemokine (especially CCR3) activity and are especially useful for treating asthma and/or rhinitis.

11 Claims, No Drawings

OTHER PUBLICATIONS

Jansson et al., "Synthesis of $^3$H and $^{14}$C Ketanserin," *Journal of Labelled Compounds and Radiopharmaceuticals* XXV(7):783-792 (1988).

STN International, File CAPLUS, CAPLUS accession No. 1996:113480, Document No. 124:220549, Kharkovskij Farmatsevticheskij Institut: Piperdylamide of 3,5-dibromo-4-aminobenzene-sulfonylaminosuccinic acid which produces neuroptic and diruetic effects; & SU, A1,1824396, 1993630.

Acs et al., "Preparation of N-(4-piperidinylbutyl)carboxamides as D3 receptor agonists for treatment of CNS and ophthalmic disorders", CAPLUS, Accession No. 2003:282395; Document No. 13S:287532, 2003, 2 pages.

Baxter, "Preparation of piperidinyl compounds as modulators of chemokine receptor activity", CAPLUS, Accession No. 2000:707161; Document No. 133:266738, 2000, 5 pages.

CAS ONLINE on STN, Chem. Abstr., Accession No. 1980:586265, Carissimi et al. Farmaco, Edizion Scientificu (1980), 35(6), 504-26, abstract only.

Emonds-Alt et al., "Preparation of N-(aminoalkyl)piperidines, their enantiomers, and pharmaceutical compositions as neurokinin receptor antagonists", CAPLUS Accession No. 1993:408684; Document No. 119:8684.

Forbes et al., "(R)-3,*N*-Dimethyl-*N*-[1-methyl-3-(4-methyl-piperidin-1-yl)propyl] benzenesulfonamide: The First Selective 5-HT$_7$ Receptor Antagonist", *J. Med. Chem.* 41(5):655-657 (1998).

King, "Bioisosteres, Conformational Restriction, and Prodrugs—Case History: An Example of a Conformational Restriction Approach", *Medicinal Chemistry: Principles and Practice* pp. 206-209 (1994).

Lopez-Rodriguez et al., "First Pharmacophoric Hypothesis for 5-HT$_7$ Antagonism", *Bioorganic & Mechanical Chem.* 10:1097-1100 (2000).

Malleron et al., "New Indole Derivatives as Potent and Selective Serotonin Uptake Inhibitors", *J. Med. Chem.* 36:1194-1202 (1993).

Nakazato et al., *Chem. Abs.* 126:8111 (WO 9629330).

Rubini et al., "Synthesis of isosteric methylene-oxy pseudodipeptide analogues as novel amide bond surrogate units", *Tetrahedron* 42:6039-6045 (1986).

\* cited by examiner

PIPERIDINE DERIVATIVES USEFUL AS MODULATORS OF CHEMOKINE RECEPTOR ACTIVITY

CROSS-REFERENCE TO RELATED APPLICATIONS

This application is the national phase application under 35 U.S.C. § 371 of PCT International Application No. PCT/SE02/01401, which has an International filing date of Jul. 19, 2002, and which designated United Kingdom Application Serial No. 0117899.5 filed Jul. 23, 2001, as priority. The contents of these applications are incorporated by reference in their entirety.

The present invention concerns piperidine derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in WO99/38514, WO99/04794 and WO00/35877.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important rôle in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C-X-C, or α) and Cys-Cys (C-C, or β) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL,8) and neutrophil-activating peptide 2 (NAP-2).

The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Histamine is a basic amine, 2-(4-imidazolyl)-ethylamine, and is formed from histidine by histidine decarboxylase. It is found in most tissues of the body, but is present in high concentrations in the lung, skin and in the gastrointestinal tract. At the cellular level inflammatory cells such as mast cells and basophils store large amounts of histamine. It is recognised that the degranulation of mast cells and basophils and the subsequent release of histamine is a fundamental mechanism responsible for the clinical manifestation of an allergic process. Histamine produces its actions by an effect on specific histamine G-protein coupled receptors, which are of three main types, H1, H2 and H3. Histamine H1 antagonists comprise the largest class of medications used in the treatment of patients with allergic disorders, especially rhinitis and urticaria Antagonists of H1 are useful in controlling the allergic response by for example blocking the action of histamine on post-capillary venule smooth muscle, resulting in decreased vascular permeability, exudation and oedema. The antagonists also produce blockade of the actions of histamine on the H1 receptors on c-type nociceptive nerve fibres, resulting in decreased itching and sneezing.

Viral infections are known to cause lung inflammation. It has been shown experimentally that the common cold increases mucosal output of eotaxin in the airways. Instillation of eotaxin into the nose can mimic some of the signs and symptoms of a common cold. (See, Greiff L et al Allergy (1999) 54(11) 1204-8 [Experimental common cold increase mucosal output of eotaxin in atopic individuals] and Kawaguchi M et al Int. Arch. Allergy Immunol. (2000) 122 S144 [Expression of eotaxin by normal airway epithelial cells after virus A infection].)

The present invention provides a compound of formula (I):

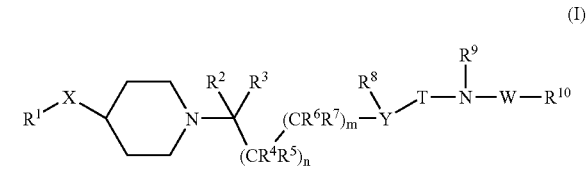

wherein:
T is C(O) or S(O)$_2$;
W is C(O) or S(O)$_2$;
X is CH$_2$, O or NH;
Y is CR$^{11}$ or N;
n is 0, 1 or 2;
m is 1 or, when Y is CR$^{11}$ m is 0;
R$^1$ is optionally substituted aryl or optionally substituted heterocyclyl;
R$^2$, R$^3$, R$^4$, R$^5$, R$^6$, R$^7$ and R$^8$ are, independently, hydrogen or C$_{1-6}$ alkyl; wherein these alkyl groups are optionally substituted by OH, provided that when Y is N then R$^8$ does not have a hydroxy on the carbon atom bonded to Y;
or R$^2$ and R$^3$, R$^4$ and R$^5$, or R$^6$ and R$^7$, together with the atom to which they are attached, form a 3-7 membered carbocyclic ring;
R$^4$ may additionally be OH or C$_{1-6}$ alkoxy;
when Y is CR$^{11}$ the group R$^6$ may additionally be OH or C$_{1-6}$ alkoxy;
provided that only one R$^4$ or R$^6$ is OH;
R$^9$ is hydrogen or C$_{1-6}$ alkyl;
R$^{10}$ is alkyl, optionally substituted aryl, optionally substituted aralkyl or optionally substituted heterocyclyl;
R$^{11}$ is hydrogen or C$_{1-6}$ alkyl;
wherein the foregoing aryl and heterocyclyl moieties are optionally substituted by:
halogen, cyano, nitro, hydroxy, oxo, S(O)$_p$R$^{12}$, OC(O)NR$^{13}$R$^{14}$, NR$^{15}$R$^{16}$, NR$^{17}$C(O)R$^{18}$, NR$^{19}$C(O)NR$^{20}$R$^{21}$, S(O)$_2$NR$^{22}$R$^{23}$, NR$^{24}$S(O)$_2$R$_{25}$, C(O)NR$^{26}$R$^{27}$ C(O)R$^{28}$, CO$_2$R$^{29}$, NR$^{30}$CO$_2$R$^{31}$, C$_{1-6}$ alkyl, CF$_3$, C$_{1-6}$ alkoxy(C$_{1-6}$)alkyl, C$_{1-6}$ alkoxy, OCF$_3$, C$_{1-6}$ alkoxy(C$_{1-6}$) alkoxy (preferably not in the form of a acetal), C$_{1-6}$ alkylthio, C$_{2-6}$ alkenyl, C$_{2-6}$ alkynyl, C$_{3-10}$ cycloalkyl (itself optionally substituted by C$_{1-4}$ alkyl or oxo), methylenedioxy, difluoromethylenedioxy, phenyl, phenyl($C_{1-4}$)alkyl, phenoxy, phenylthio, phenyl($C_{1-4}$) alkoxy, heteroaryl, heteroaryl($C_{1-4}$)alkyl, heteroaryloxy or heteroaryl($C_{1-4}$)alkoxy;

wherein any of the immediately foregoing phenyl and heteroaryl moieties are optionally substituted with halogen, hydroxy, nitro, S(O)q($C_{1-4}$ alkyl), S(O)$_2$NH$_2$, cyano, $C_{1-4}$ alkyl, $C_{1-4}$ alkoxy, C(O)NH$_2$, C(O)NH($C_{1-4}$ alkyl), CO$_2$H, CO$_2$($C_{1-4}$ alkyl), NHC(O)($C_{1-4}$ alkyl), NHS(O)$_2$($C_{1-4}$ alkyl), C(O)($C_{1-4}$ alkyl), CF$_3$ or OCF$_3$;

p and q are, independently, 0, 1 or 2;

$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{26}$, $R^{27}$, $R^{28}$, $R^{29}$, and $R^{30}$ are, independently, hydrogen, $C_{1-6}$ alkyl (optionally substituted by halogen, hydroxy or $C_{3-10}$ cycloalkyl), CH$_2$($C_{2-6}$ alkenyl), phenyl (itself optionally substituted by halogen, hydroxy, nitro, NH2, NH($C_{1-4}$ alkyl), N($C_{1-4}$ alkyl)$_2$, S(O)$_2$($C_{1-4}$ alkyl), S(O)$_2$NH$_2$, S(O)NH($C_{1-4}$ alkyl), S(O)$_2$N($C_{1-4}$ alkyl)$_2$, cyano, $C_{1-4}$ alkyl, $C_{1-4}$ alkoxy, C(O)NH$_2$, C(O)NH($C_{1-4}$ alkyl), C(O)N ($C_{1-4}$ alkyl)$_2$, CO$_2$H, CO$_2$($C_{1-4}$ alkyl), NHC(O) ($C_{1-4}$ alkyl), NHS(O)$_2$($C_{1-4}$ alkyl), C(O)($C_{1-4}$ alkyl), CF$_3$ or OCF$_3$) or heterocyclyl (itself optionally substituted by halogen, hydroxy, nitro, NH2, NH($C_{1-4}$ alkyl), N($C_{1-4}$ alkyl)$_2$, S(O)$_2$($C_{1-4}$ alkyl), S(O)$_2$NH$_2$, S(O)$_2$NH($C_{1-4}$ alkyl), S(O)$_2$N($C_{1-4}$ alkyl)$_2$, cyano, $C_{1-4}$ alkyl, $C_{1-4}$ alkoxy, C(O)NH$_2$, C(O)NH($C_{1-4}$ alkyl), C(O)N($C_{1-4}$ alkyl)$_2$, CO$_2$H, CO$_2$($C_{1-4}$ alkyl), NHC(O)($C_{1-4}$ alkyl), NHS(O)$_2$($C_{1-4}$ alkyl), C(O)($C_{1-4}$ alkyl), CF$_3$ or OCF$_3$);

alternatively NR$^{13}$R$^{14}$, NR$^{15}$R$^{16}$, NR$^{20}$R$^{21}$, R$^{23}$, NR$^{26}$NR$^{27}$, and N($C_{1-4}$ alkyl)$_2$ may, independently, form a 4-7 membered heterocyclic ring, azetidine, pyrrolidine, piperidine, azepine, 1,4-morpholine or 1,4-piperazine, the latter optionally substituted by $C_{1-4}$alkyl on the distal nitrogen;

$R^{12}$, $R^{25}$ and $R^{31}$ are, independently, $C_{1-6}$ alkyl (optionally substituted by halogen, hydroxy or $C_{3-10}$ cycloalkyl), CH$_2$($C_{2-6}$ alkenyl), phenyl (itself optionally substituted by halogen, hydroxy, nitro, NH$_2$, NH($C_{1-4}$ alkyl), N($C_{1-4}$ alkyl)$_2$ (and these alkyl groups may join to form a ring as described for $R^{13}$ and $R^{14}$ above), S(O)$_2$($C_{1-4}$ alkyl), S(O)$_2$NH$_2$, S(O)$_2$NH(CH$_{1-4}$ alkyl), S(O)$_2$N($C_{1-4}$ alkyl)$_2$ (and these alkyl groups may join to form a ring as described for $R^{13}$ and $R^{14}$ above), cyano, $C_{1-4}$ alkyl, $C_{1-4}$ alkoxy, C(O)NH$_2$, C(O)NH($C_{1-4}$ alkyl), C(O)N($C_{1-4}$ alkyl)$_2$ (and these alkyl groups may join to form a ring as described for $R^{13}$ and $R^{14}$ above), CO$_2$H, CO$_2$($C_{1-4}$ alkyl), NHC(O)($C_{1-4}$ alkyl), NHS(O)$_2$($C_{1-4}$ alkyl), C(O)($C_{1-4}$ alkyl), CF$_3$ or OCF$_3$) or heterocyclyl (itself optionally substituted by halogen, hydroxy, nitro, NH$_2$, NH($C_{1-4}$ alkyl), N($C_{1-4}$ alkyl)$_2$ (and these alkyl groups may join to form a ring as described for $R^{13}$ and $R^{14}$ above), S(O)$_2$ ($C_{1-4}$ alkyl), S(O)$_2$NH$_2$, S(O)$_2$NH($C_{1-4}$ alkyl), S(O)$_2$N ($C_{1-4}$ alkyl)$_2$ (and these alkyl groups may join to form a ring as described for $R^{13}$ and $R^{14}$ above), cyano, $C_{1-4}$ alkyl, $C_{1-4}$ alkoxy, C(O)NH$_2$, C(O)NH($C_{1-4}$ alkyl), C(O)N($C_{1-4}$ alkyl)$_2$ (and these alkyl groups may join to form a ring as described for $R^{13}$ and $R^{14}$ above), CO$_2$H, CO$_2$ ($C_{1-4}$ alkyl), NHC(O)($C_{1-4}$ alkyl), NHS(O)$_2$($C_{1-4}$ alkyl), C(O)($C_{1-4}$ alkyl), CF$_3$ or OCF$_3$);

or an N-oxide thereof; or a pharmaceutically acceptable salt thereof; or a solvate thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, dihydrochloride, hydrobromide, phosphate, sulfate, acetate, diacetate, fumarate, maleate, tartrate, citrate, oxalate, methanesulfonate or p-toluenesulfonate. Salts also include metal salts, such as alkali metal salts (for example a sodium salt).

The compounds of the invention may exist as solvates (such as hydrates) and the present invention covers all such solvates.

Halogen includes fluorine, chlorine, bromine and iodine.

Alkyl groups and moieties are straight or branched chain and are, for example, methyl, ethyl, n-propyl, iso-propyl or tert-butyl. The term 'butyl' without any indication of branching is a straight chain (that is n-butyl).

Alkenyl is, for example, vinyl or allyl.

Alkynyl is, for example, propargyl.

Haloalkyl is preferably CF$_3$. Haloalkoxy is preferably OCF$_3$.

Cycloalkyl is mono-, bi or tricyclic and is, for example, cyclopropyl, cyclopentyl, cyclohexyl, norbornyl or camphoryl. The cycloalkyl ring is optionally fused to a benzene ring (for example forming a bicyclo[4.2.0]octa-1,3,5-trienyl or indanyl ring system).

3-7 Membered carbocyclic rings are preferably monocyclic and include cyclopropyl, cyclopentyl and cyclohexyl.

Aryl is preferably phenyl or naphthyl.

Arylalkyl is, for example aryl($C_{1-4}$)alkyl, such as benzyl or 2-phenylethyl.

Heterocyclyl is an aromatic or non-aromatic 5 or 6 membered ring, optionally fused to one or more other rings, comprising at least one heteroatom selected from the group comprising nitrogen, oxygen and sulfur; or an N-oxide thereof, or an S-oxide or S-dioxide thereof. Heterocyclyl is, for example, furyl, thienyl (also known as thiophenyl), pyrrolyl, 2,5-dihydropyrrolyl, thiazolyl, pyrazolyl, oxazolyl, isoxazolyl, imidazolyl, piperidinyl, morpholinyl, pyridinyl (for example in 6-oxo-1,6-dihydro-pyridinyl), pyrimidinyl, indolyl, 2,3-dihydroindolyl, benzo[b]furyl (also known as benzfuryl), benz[b]thienyl (also known as benzthienyl or benzthiophenyl), 2,3-dihydrobenz[b]thienyl (for example in 1,1-dioxo-2,3-dihydrobenz[b]thienyl), indazolyl, benzimidazolyl, benztriazolyl, benzoxazolyl, benzthiazolyl (for example in 1H-benzthiazol-2-one-yl), 2,3-dihydrobenzthiazolyl (for example in 2,3-dihydrobenzthiazol-2-one-yl), 1,2,3-benzothiadiazolyl, an imidazopyridinyl (such as imidazo [1,2a]pyridinyl), thieno[3,2-b]pyridin-6-yl-1,2,3-benzoxadiazolyl (also known as benzo[1,2,3]thiadiazolyl), 2,1,3-benzothiadiazolyl, benzofurazan (also known as 2,1,3-benzoxadiazolyl), quinoxalinyl, dihydro-1-benzopyryliumyl (for example in a coumarinyl or a chromonyl), 3,4-dihydro-1H-2,1-benzothiazinyl (for example in 2-dioxo-3,4-dihydro-1H-2,1-benzothiazinyl), a pyrazolopyridine (for example 1H-pyrazolo[3,4-b]pyridinyl), a purine (for example in 3,7-dihydro-purin-2,6-dione-8-yl), quinolinyl, isoquinolinyl (for example in 2H-isoquinolin-1-one-yl), a naphthyridinyl (for example [1,6]naphthyridinyl or [1,8] naphthyridinyl or in 1H-[1,8]naphthyridinone-yl), a benzothiazinyl (for example in 4H-benzo[1,4]thiazin-3-one-yl), benzo[d]imidazo[2,1-b]thiazol-2-yl or dibenzothiophenyl (also known as dibenzothienyl); or an N-oxide thereof (such as a pyridine N-oxide), or an S-oxide or S-dioxide thereof.

An N-oxide of a compound of formula (I) is, for example, a 1-oxido-piperidinyl compound.

The present invention provides a compound of formula (I) wherein; T is C(O) or S(O)$_2$; W is C(O) or S(O)$_2$; X is CH$_2$, O or NH; Y is CR$^{11}$ or N; n is 0, 1 or 2 m is 1 or, when Y is CR$^{11}$ m is 0; R$^1$ is optionally substituted aryl or optionally substituted heterocyclyl; R$^2$, R$^3$, R$^4$, R$^5$, R$^6$, R$^7$ and R$^8$ are, independently, hydrogen or $C_{1-6}$ alkyl; wherein these alkyl groups are optionally substituted by OH, provided that when Y is N then $R^8$ does not have a hydroxy on the carbon atom bonded to Y; or $R^2$ and $R^3$, $R^4$ and $R^5$, or $R^6$ and $R^7$, together with the atom to which they are attached, form a 3-7 membered carbocyclic ring; $R^4$ may additionally be OH or $C_{1-6}$ alkoxy; when Y is $CR^{11}$ the group $R^6$ may additionally be OH or $C_{1-6}$ alkoxy; provided that only one $R^4$ or $R^6$ is OH; $R^9$ is hydrogen or $C_{1-6}$ alkyl; $R^{10}$ is alkyl, optionally substituted aryl, optionally substituted aralkyl or optionally substituted heterocyclyl; $R^{11}$ is hydrogen or $C_{1-6}$ alkyl; wherein the foregoing aryl and heterocyclyl moieties are optionally substituted by: halogen, cyano, nitro, hydroxy, oxo, $S(O)_pR^2$, $OC(O)NR^{13}R^{14}$, $NR^{15}R^{16}$, $NR^{17}C(O)R^{18}$, $NR^{19}C(O)NR^{20}R^{21}$, $S(O)_2NR^{22}R^{23}$, $NR^{24}S(O)_2R^{25}$, $C(O)NR^{26}R^{27}$, $C(O)R^{28}$, $CO_2R^{29}$, $NR^{30}CO_2R^{31}$, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkoxy($C_{1-6}$)alkoxy, $C_{1-6}$ alkylthio, $C_{1-6}$ haloalkylthio, $C_{2-6}$ alkenyl, $C_{2-6}$ alkynyl, $C_{3-10}$ cycloalkly, (itself optionally substituted by $C_{1-4}$ alkyl or oxo), methylenedioxy, difluoromethylenedioxy, phenyl, phenyl($C_{1-4}$) alkyl, phenoxy, phenylthio, phenyl($C_{1-4}$)alkbxy, heteroaryl, heteroaryl($C_{1-4}$)alkyl, heteroaryloxy or heteroaryl($C_{1-4}$) alkoxy; wherein any of the immediately foregoing phenyl and heteroaryl moieties are optionally substituted with halogen, hydroxy, nitro, $S(O)_q(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$; p and q are, irndependently, 0, 1 or 2; $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{26}$, $R^{27}$, $R^{28}$, $R^{29}$, and $R^{30}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ allyl)$_2$, $S(O)_2(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ aLkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); alternatively $NR^{13}R^{14}$, $NR^{15}R^{16}$, $NR^{20}R^{21}$, $NR^{22}R^{23}$, $NR^{26}R^{27}$, may, independently, form a 4-7 membered heterocyclic ring, azetidine, pyrrolidine, piperidine, azepine, 1,4-morpholine or 1,4-piperazine, the latter optionally substituted by $C_{1-4}$alkyl on the distal nitrogen; $R^{12}$, $R^{25}$ and $R^{31}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^{13}$ and $R^{14}$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^{13}$ and $R^{14}$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^{13}$ and $R^{14}$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^{13}$ and $R^{14}$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^{13}$ and $R^{14}$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^{13}$ and $R^{14}$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); or an N-oxide thereof; or a pharmaceutically acceptable salt thereof; or a solvate thereof.

In another aspect X is O.

In another aspect $R^1$ is phenyl substituted with one or more of fluorine, chlorine, $C_{1-4}$ alkyl (especially methyl) or $C_{1-4}$ alkoxy (especially methoxy).

In a further aspect $R^1$ is phenyl optionally substituted (for example with one, two or three of) by halogen (especially fluoro or chloro), $C_{1-4}$ alkyl (especially methyl) or $C_{1-4}$ alkoxy (especially methoxy). In a still further aspect $R^1$ is phenyl substituted by one, two or three of: fluoro, chloro, methyl or methoxy. In another aspect $R^1$ is phenyl optionally substituted by halogen (especially fluoro or chloro), $C_{1-4}$ alkyl (especially methyl); especially optionally substituted (for example independently with one, two or three of, especially two or three of) by fluoro, chloro or methyl. In a still further aspect $R^1$ is 3,4-dichlorophenyl, or, additionally 2-chloro4fluorophenyl, 2-methyl4-chlorophenyl, 2,4-dichloro-3-methylphenyl or 3,4-dichloro-2-methylphenyl.

In another aspect one of T and W is C(O) and the other is $S(O)_2$.

In a still further aspect T is is C(O).

In another aspect W is $S(O)_2$.

In another aspect $R^{11}$ is hydrogen.

In yet another aspect Y is CH or N. In one aspect Y is N. In another aspect Y is CH.

In yet another aspect $R^2$ is hydrogen or methyl; for example $R^2$ is hydrogen.

In a further aspect $R^3$ is hydrogen.

In another aspect of the invention m is 0 or 1; especially 1.

In a still further aspect n is 0 or 1; n is especially 1.

In another aspect $R^4$ is hydrogen, methyl, ethyl or hydroxy; for example it is hydrogen or hydroxy.

In yet another aspect $R^5$, $R^6$ and $R^7$ are, independently, hydrogen, methyl or ethyl (particularly hydrogen or methyl, for example they are all hydrogen).

In yet another aspect $R^8$ and $R^9$ are both hydrogen.

In a further aspect $R^2$, $R^3$, $R^4$, $R^5$, $R^6$, $R^7$, $R^8$ and $R^9$ are all hydrogen.

In a still further aspect $R^{10}$ is unsubstituted phenyl, mono-substituted phenyl, unsubstituted heterocyclyl or mono-substituted heterocyclyl, the substituents being chosen from those described above.

In another aspect $R^{10}$ is phenyl substituted with halogen, alkyl or alkoxy; especially halogen (for example fluoro or chloro), $C_{1-4}$ alkyl (for example methyl) or $C_{1-4}$ alkoxy (for example methoxy).

In yet another aspect $R^{10}$ is phenyl or heterocyclyl, either of which is optionally substituted by: halo, hydroxy, nitro, cyano, oxo, amino, $C_{1-4}$ alkyl (itself optionally substituted by $S(O)_2(C_{1-4}$kyl), $S(O)_2$phenyl), $C_{1-4}$ alkoxy, $S(O)_kR^{32}$ (wherein k is 0, 1 or 2 (preferably 2); and $R^{32}$ is $C_{1-4}$ alkyl, $C_{1-4}$ hydroxyalkyl, $C_{3-7}$ cycloalkyl($C_{1-4}$ alkyl) (such as cyclopropylmethyl) or phenyl), $C_{1-4}$ haloalkylthio, $C(O)NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl)$_2$.

In another aspect $R^{10}$ is phenyl or heterocyclyl, either of which is optionally substituted by: halo, hydroxy, nitro, cyano, oxo, amino, $C_{1-4}$ alkyl (itself optionally substituted by $S(O)_2(C_{1-4}$ alkyl), $S(O)_2$phenyl), $C_{1-4}$ alkoxy, $S(O)_kR^{32}$ (wherein k is 0, 1 or 2 (preferably 2); and $R^{32}$ is $C_{1-4}$ alkyl, $C_{1-4}$ hydroxyalkyl, $C_{3-7}$ cycloalkyl($C_{1-4}$ alkyl) (such as cyclopropylmethyl) or phenyl), C(O)NH$_2$, NHS(O)$_2$(C$_{1-4}$ alkyl), S(O)$_2$NH$_2$, S(O)$_2$NH(C$_{1-4}$ alkyl) or S(O)$_2$N(C$_{1-4}$ alkyl)$_2$.

In one aspect the variable R$^{10}$ is phenyl optionally substituted by: halo, hydroxy, nitro, cyano, amino, C$_{1-4}$ alkyl (itself optionally substituted by S(O)$_2$(C$_{1-4}$ alkyl), S(O)$_2$phenyl), C$_{1-4}$ alkoxy, S(O)$_k$R$^{32}$ (wherein k is 0, 1 or 2 (preferably 2); and R$^{32}$ is C$_{1-4}$ alkyl, C$_{1-4}$ hydroxyalkyl, C$_{3-7}$ cycloalkyl(C$_{1-4}$ alkyl) (such as cyclopropylmethyl) or phenyl), C$_{1-4}$ haloalkylthio, C(O)NH$_2$, NHS(O)$_2$(C$_{1-4}$ alkyl), S(O)$_2$NH$_2$, S(O)$_2$NH(C$_{1-4}$ alkyl) or S(O)$_2$N(C$_{1-4}$ alkyl)$_2$ (and these alkyl groups may join to form a ring as described for R$^{13}$ and R$^{14}$ above).

In another aspect the variable R$^{10}$ is phenyl optionally substituted by: halo, hydroxy, nitro, cyano, amino, C$_{1-4}$ alkyl (itself optionally substituted by S(O)$_2$(C$_{1-4}$ alkyl), S(O)$_2$phenyl), C$_{1-4}$ alkoxy, S(O)$_k$R$^{32}$ (wherein k is 0, 1 or 2 (preferably 2); and R$^{32}$ is C$_{1-4}$ alkyl, C$_{1-4}$ hydroxyalkyl, C$_{3-7}$ cycloalkyl(C$_{1-4}$ alkyl) (such as cyclopropylmethyl) or phenyl), C(O)NH$_2$, NHS(O)$_2$(C$_{1-4}$ alkyl), S(O)$_2$NH$_2$, S(O)$_2$NH(C$_{1-4}$ alkyl) or S(O)$_2$N(C$_{1-4}$ alkyl)$_2$ (and these alkyl groups may join to form a ring as described for R$^{13}$ and R$^{14}$ above).

In yet another aspect the variable R$^{10}$ is phenyl optionally substituted by: halo, hydroxy, nitro, cyano, amino, C$_{1-4}$ alkyl (itself optionally substituted by S(O)$_2$phenyl), C$_{1-4}$ alkoxy, S(O)$_k$R$^{32}$ (wherein k is 0, 1 or 2; and R$^{32}$ is C$_{1-4}$ alkyl or phenyl) or C$_{1-4}$ haloalkylthio.

In a further aspect the variable R$^{10}$ is phenyl optionally substituted by: halo, hydroxy, nitro, cyano, amino, C$_{1-4}$ alkyl (itself optionally substituted by S(O)$_2$phenyl), C$_{1-4}$ alkoxy or S(O)$_k$R$^{32}$ (wherein k is 0, 1 or 2; and R$^{32}$ is C$_{1-4}$ alkyl or phenyl).

In a still further aspect the present invention provides a compound of formula (I) wherein R$^{10}$ is phenyl optionally substituted by halogen (such as fluoro or chloro), C$_{1-4}$ alkyl (for example methyl), CF$_3$ or CO$_2$(C$_{1-4}$ alkyl) (for example CO$_2$CH$_3$); {especially R$^{10}$ substituted with halogen (for example chloro of fluoro) or C$_{1-4}$ alkyl (for example methyl)}. The variable R$^{10}$ may also be thienyl or pyridyl.

Compounds of formula (Ia), (Ia'), (Ib), (Ic) and (Id) are examples of compounds of formula (I).

In a still further aspect the present invention provides a compound of formula (Ia):

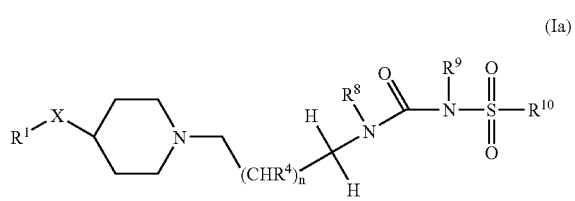
(Ia)

wherein: X, n, R$^1$, R$^4$, R$^8$, R$^9$ and R$^{10}$ are as defined above; or a pharmaceutically acceptable salt thereof.

In yet another aspect the present invention provides a compound of formnula (Ia'):

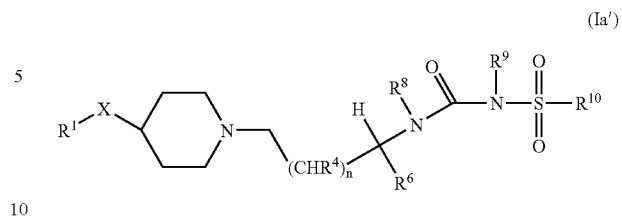
(Ia')

wherein: X, n, R$^1$, R$^4$, R$^6$, R$^8$, R$^9$ and R$^{10}$ are as defined above; or a pharmaceutically acceptable salt thereof.

In another aspect the present invention provides a compound of formula (Ib):

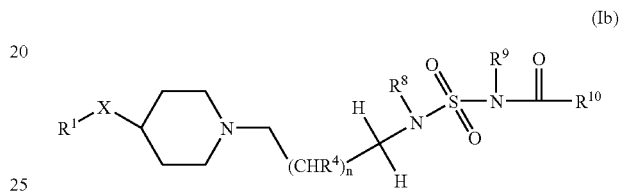
(Ib)

wherein: X, n, R$^1$, R$^4$, R$^8$, R$^9$ and R$^{10}$ are as defined above; or a pharmaceutically acceptable salt thereof.

In a further aspect the present invention provides a compound of formula (Ic):

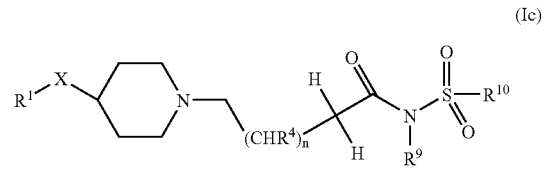
(Ic)

wherein: X, n, R$^1$, R$^4$, R$^9$ and R$^{10}$ are as defined above; or a pharmaceutically acceptable salt thereof.

In a still further aspect the present invention provides a compound of formula (Id):

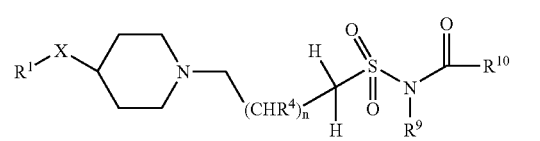
(Id)

wherein: X, n, R$^1$, R$^4$, R$^9$ and R$^{10}$ are as defined above; or a pharmaceutically acceptable salt thereof.

The compounds of formula (1) (for example compounds of formula (Ia), (Ia'), (Ib), (Ic) and (Id)) can be prepared by adaptation of methods known in the art, by the methods recited below or by methods analogous to the method of Example 1.

A compound of formula (I), wherein R$^9$ is hydrogen, T is C(O) and Y is N, can be prepared by reacting a compound of formula (II):

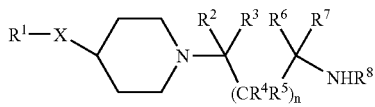

(II)

with an isocyanate of formula $R^{10}$ WN=C=O in the presence of a suitable solvent at a suitable temperature (such as room temperature). Isocyanates of formula $R^{10}$WN=C=O are commercially available or can be prepared by optional adaptation of methods described in the literature.

Alternatively a compound of formula (I), wherein $R^9$ is hydrogen, T is C(O) and Y is N, can be prepared by reacting a compound of formula (II) with the adduct formed between p-nitrophenyl chloroformate and an amide $R^{10}$WNH$_2$ in the presence of DMAP.

A compound of formula (II) can be prepared by deprotecting a compound of formula (III):

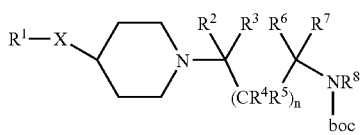

(III)

for example using trifluoroacetic acid in a suitable solvent (such as dichloromethane) or using a source of hydrogen chloride in a suitable solvent (such as dioxane).

A compound of formula (III), wherein $R^2$ is hydrogen, can be prepared by reacting a compound of formula (IV):

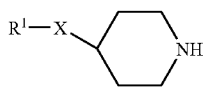

(IV)

with a compound of formula (V):

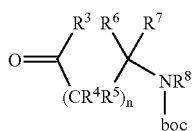

(V)

in the presence of NaBH(OAc)$_3$ and acetic acid.

A compound of formula (III), wherein $R^2$ is $C_{1-6}$ alkyl, can be prepared by reacting a compound of formula (XVII):

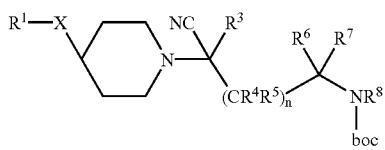

(XVII)

with a Grignard reagent of formula $R^2$MgHal (wherein Hal is chlorine, bromine or iodine) in a suitable solvent, such as tetrahydrofuran.

A compound of formula (XVII) can be prepared by reacting a compound of formula (IV) with a compound of formula (V) in the presence of titanium tetrisopropoxide, for example in dichloroethane, followed by the addition of diethylaluminium cyanide to a solution, for example in toluene.

A compound of formula (I), wherein $R^9$ is hydrogen, T is S(O)$_2$, W is C(O) and Y is N, can be prepared by reacting a compound of formula (IX):

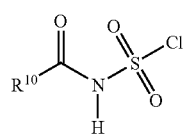

(IX)

with a compound of formula (II) in the presence of a suitable base (such as triethylamine) in a suitable solvent (such as tetrahydrofuran) at a suitable temperature (such as at, or below, room temperature). A compound of formula (IX) can be prepared by reacting an acid $R^{10}$CO$_2$H with ClS(O)$_2$N=C=O, for. example below 80° C.

A compound of formula (I) wherein T and W are both S(O)$_2$ and Y is N, can be prepared by reacting a compound of formula (X):

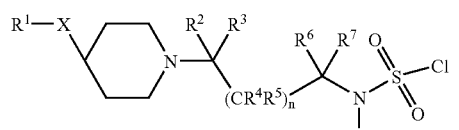

(X)

with a sulfonamide $R^{10}$S(O)$_2$NHR$^9$ in the presence of a base (such as calcium oxide), in a suitable solvent (such as DMSO) at a temperature preferably in the range 50-110° C. (For example see DE 1618439; DE 1249259; Chemical Abstracts1967, 67, 116716a). A compound of formula (X) can be prepared by reacting a compound of formula (II) with S(O)$_2$C$_{12}$ in the presence of a suitable base (such as triethylamine).

A compound of formula (I) wherein T and W are both S(O)$_2$ and Y is N, can be prepared by reacting a compound of formula (Xa):

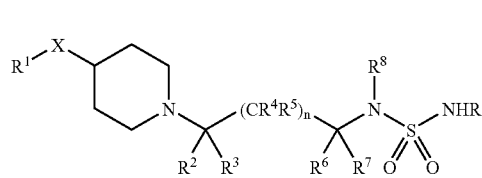

(Xa)

with a sulfonyl chloride $R^{10}$SO$_2$Cl in the presence of a base (such as calcium oxide), in a suitable solvent (such as DMSO) at a temperature preferably in the range 50-110° C.

A compound of formula (I) wherein T is S(O)$_2$, W is CO and Y is N, can be prepared by reacting a compound of formula (Xa) with an acid $R^{10}COOH$ in the presence of an appropriate coupling agent (such as ethyl dimethylaminopropyl carbodiimide (EDCI), with 4-dimethylaminopyridine (DMAP) and 1-hydroxybenzotriazole (HOBT)) in a suitable solvent, for example DMF.

A compound of formula (I) wherein $R^2$ is hydrogen, T is C(O), W is $S(O)_2$ and Y is $CR^{11}$, can be prepared by firstly hydrolysing a compound of formula (XI):

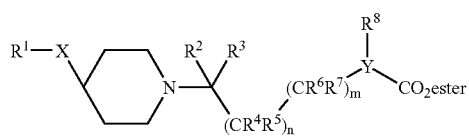

(XI)

wherein suitable ester groups include $C_{1-6}$ alkyl groups, and reacting the product so formed with $R^{10}S(O)_2NHR^9$ in the presence of an appropriate coupling agent (such as ethyl dimethylaminopropyl carbodiimide (EDCI), with 4-dimethylaminopyridine (DMAP) and 1-hydroxybenzotriazole (HOBT)) in a suitable solvent, for example DMF.

A compound of formula (XI) where $R^2$ is H can be prepared by-reductively aminating a compound of formula (XII):

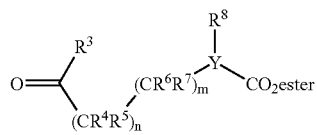

(XII)

with a compound of formula (XII):

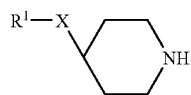

(XIII)

Alternatively a compound of formula (XI) where $R^2$ and $R^3$ are both H can be prepared by reaction of a compound of formula (XIIa):

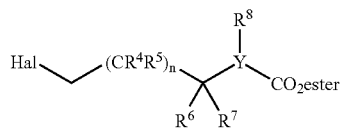

(XIIa)

with a compound of formula (XIII) in the presence of a base, for example potassium carbonate, in a suitable solvent, for example acetone at reflux.

Alternatiyely a compound of formula (XI) where $R^2$ and $R^8$ are H, n and m are 0 and Y is $CR^{11}$ can be prepared by by reaction of a compound of formula (XIIb):

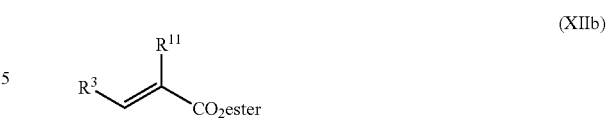

(XIIb)

with a compound of formula (XIII) in the presence of a base, for example sodium hydroxide, in a suitable solvent, for example THF, for example at room temperature.

A compound of formula (XI), wherein $R^2$ is $C_{1-6}$ alkyl, can be prepared by reacting a compound of formula (XVIII):

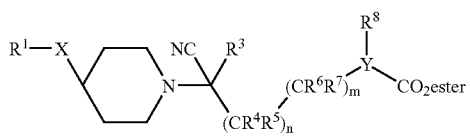

(XVIII)

with a Grignard reagent of formula $R^2MgHal$ (wherein Hal is chlorine, bromine or iodine) in a suitable solvent, such as tetrahydrofuran.

A compound of formula (XVIII) can be prepared by reacting a compound of formula (XII) with a compound of formula (XIII) in the presence of titanium tetrisopropoxide, for example in dichloroethane, followed by the addition of diethylaluminium cyanide to a solution, for example in toluene.

A compound of formula (I), wherein T and W are both C(O) and Y is $CR^{11}$, can be prepared by heating a compound of formula (XIV):

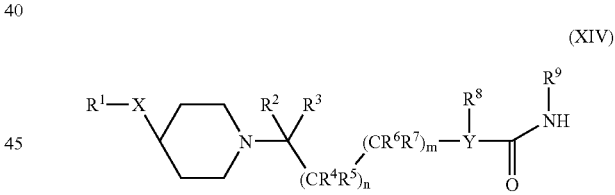

(XIV)

in the presence of $R^{10}C(OR')_2N(CH_3)_2$ or $R^{10}C(OR')_3$, wherein R' is methyl or ethyl, or $(OR')_3$ is $(OCH_2)_3CCH_3$. A compound of formula (XIV) can be prepared by firstly hydrolysing a compound of formula (XI) and then coupling the product so formed with an amine $R^3NH_2$ in the presence of an appropriate coupling agent (such as ethyl dimethylaminopropyl carbodiimide, with 4dimethylaminopyridine and 1-hydroxybenzotriazole) in a suitable solvent, for example DMF.

A compound of formula (I) where $R^9$ is alkyl may be prepared by alkylation of a compound of formula (I) where $R^9$ is H by using an appropriate alkylating agent $R^9$-L, wherein L is a leaving group (such as triflate, a halide or a diazo group) in the presence of a suitable base (such as sodium hydride) in a suitable solvent.

A compound of formula (XV) can be prepared by reductively aminating a compound of formula (XVI):

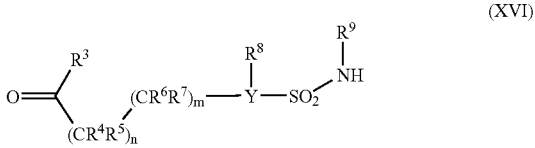
(XVI)

with a compound of formula (IV) to obtain a compound wherein $R^2$ is hydrogen, or aminonitrile formation followed by a Grignard reaction to obtain a compound wherein $R^2$ is alkyl.

A compound of formula (XVI) can be prepared by reacting (when Y is $CR^{11}$)

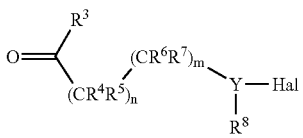

with $Na_2SO_3$ in aqueous acetone followed by activation of the sulfonic acid, for example by chlorination with $POCl_3$ and then reaction with an amine, $R^9NH_2$.

When Y is N a compound of formula (XVI) can be obtained by hearting a compound of formula (XVII):

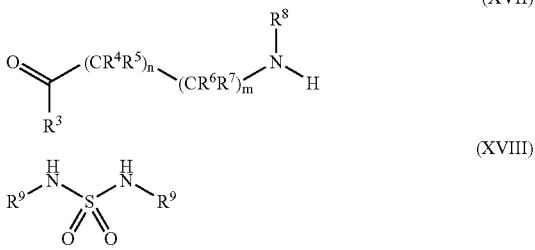
(XVII)

(XVIII)

with a compound of formula (XVIII), for example in dioxan, for example at reflux.

Further compounds of formula (I) can be prepared by adaptation of: the routes described above, methods described in the art or the Examples recited below. The intermediates identified above are commercially available or can be prepared by using or adapting methods described in the art.

In another aspect the present invention provides processes for the preparation of compound of formula (I) (for example compounds of formula (Ia), (Ia'), (Ib), (Ic) and (Id)).

The intermediates of formula (X) and (XV) defined herein are novel and these, and processes for their preparation, are provided as further features of the invention.

The compounds of the invention have activity as pharmaceuticals, in particular as modulators of chemokine receptor (especially CCR3) activity, and may be used in the treatment of autoimmune, inflammatory, proliferative or hyperproliferative diseases, or immunologically-mediated diseases (including rejection of transplanted organs or tissues and Acquired in unodeficiency Syndrome (AIDS)).

In one aspect examples of these conditions are:
(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;
(2) (bone and joints) arthrides including rheumatic, infectious, autoimmune, seronegative spondyloarthropathies (such as ankylosing spondylitis, psoriatic arthritis or Reiter's disease), Behget's disease, Sjogren's syndrome or systemic sclerosis;
(3) (skin and eyes) psoriasis, atopic dermatitis, contact dermatitis or other eczrnatous dermitides, seborrhoetic dermatitis, Lichen planus, Phemphigus, bullous Phemphigus, Epidermolysis bullosa, urticaria, angiodermas, vasculitides erythemas, cutaneous eosinopbiiias, uveitis, Alopecia areata or vernal conjunctivitis;
(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);
(5) (Allograft rejection) acute and chronic following, for example, transplantation of kidney, heart, liver, lung, bone marrow, skin or cornea; or chronic graft versus host disease; and/or
(6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, Sezary syndrome, idiopathic thrombocytopenia pupura or disorders of the menstrual cycle.

The compounds of the invention are also. H1 antagonists and may be used in the treatment of allergic disorders.

The compounds of the invention may also be used to control a sign and/or symptom of what is commonly referred to as a cold (for example a sign and/or symptom of a common cold or influenza or other associated respiratory virus infection).

According to a further feature of the invention there is provided a compound of formula (I) (for example a compound of formula (Ia), (Ia'), (Ib), (Ic) or (Id)), or a pharmaceutically acceptable salt thereof or a solvate thereof, for use in a method of treatment of a warm blooded animal (such as man) by therapy (including prophylaxis).

According to a further feature of the present invention there is provided a method for modulating chemokine receptor activity (especially CCR3 receptor activity), or antagonising H1, in a warm blooded animal, such as man, in need of such treatment, which comprises administering to said animal an effective amount of a compound of the formula (I)

(for example a compound of formula (Ia), (Ia'), (Ib), (Ic) or (Id)), or a pharmaceutically acceptable salt thereof or a solvate thereof.

The invention also provides a compound of the formula (I) (for example a compound of formula (Ia), (Ia'), (Ib), (Ic) or (Id)), or a pharmaceutically acceptable salt thereof or a solvate thereof, for use as a medicament.

In another aspect the invention provides the use of a compound of formula (I) (for example a compound of formula (Ia), (Ia'), (Ib), (Ic) or (Id)), or a pharmaceutically acceptable salt thereof or a solvate thereof, in the manufacture of a medicament for use in therapy (for example modulating chemokine receptor activity (especially CCR3 receptor activity), or antagonising H1, in a warm blooded animal, such as man).

The invention further provides the use of a compound of formula (I) (for example a compound of formula (Ia), (Ia'), (Ib), (Ic) or (Id)), or a pharmaceutically acceptable salt thereof, in the manufacture of a medicament for use in the treatment of:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle; in a warm blooded animal, such as man.

In a further aspect a compound of formula (I) (for example a compound of formula (Ia), (Ia'), (Ib), (Ic) or (Id)), or a pharmaceutically acceptable salt thereof, is useful in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis}.

In a still further aspect a compound of formula (I) (for example a compound of formula (Ia), (Ia'), (Ib), (Ic) or (Id)), or a pharmaceutically acceptable salt thereof, is useful in the treatment of asthma.

The present invention also provides the use of a compound of formula (I) (for example a compound of formula (Ia), (Ia'), (Ib), (Ic) or (Id)), or a pharmaceutically acceptable salt thereof, in the manufacture of a medicament for use in the treatment of asthma or rhinitis.

The present invention further provides a method of treating a chemokine mediated disease state (especially a CCR3 mediated disease state, especially asthma) in a warm blooded mammal, such as man, which comprises administering to a mammal in need of such treatment an effective amount of a compound of formula (I) (for example a compound of formula (Ia), (Ia'), (Ib), (Ic) or (Id)), or a pharmaceutically acceptable salt thereof or solvate thereof.

In order to use a compound of the invention, or a pharmaceutically acceptable salt thereof or solvate thereof, for the therapeutic treatment of a warm blooded animal, such as man, in particular modulating chemokine receptor (for example CCR3 receptor) activity or antagonising H1, said ingredient is normally formulated in accordance with standard pharmaceutical practice as a pharmaceutical composition.

Therefore in another aspect the present invention provides a pharmaceutical composition which comprises a compound of the formula (I) (for example a compound of formula (Ia), (Ia'), (Ib), (Ic) or (Id)), or a pharmaceutically acceptable salt thereof or a solvate thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid)

emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 mgkg$^{-1}$ to 100 mgkg$^{-1}$ of the compound, preferably in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (I) (for example a compound of formula (Ia), (Ia'), (Ib), (Ic) or (Id)), or a pharmaceutically-acceptable salt thereof (hereafter Compound X), for therapeutic or prophylactic use in humans:

(a)

| Tablet I | mg/tablet |
|---|---|
| Compound X | 100 |
| Lactose Ph. Eur. | 179 |
| Croscarmellose sodium | 12.0 |
| Polyvinylpyrrolidone | 6 |
| Magnesium stearate | 3.0 |

(b)

| Tablet II | mg/tablet |
|---|---|
| Compound X | 50 |
| Lactose Ph. Eur. | 229 |
| Croscarmellose sodium | 12.0 |
| Polyvinylpyrrolidone | 6 |
| Magnesium stearate | 3.0 |

(c)

| Tablet III | mg/tablet |
|---|---|
| Compound X | 1.0 |
| Lactose Ph. Eur. | 92 |
| Croscarmellose sodium | 4.0 |
| Polyvinylpyrrolidone | 2.0 |
| Magnesium stearate | 1.0 |

(d)

| Capsule | mg/capsule |
|---|---|
| Compound X | 10 |
| Lactose Ph. Eur. | 389 |
| Croscarmellose sodium | 100 |
| Magnesium stearate | 1.0 |

(e)

| Injection I | (50 mg/ml) |
|---|---|
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. The tablets (a)-(c) may be enteric coated by conventional means, for example to provide a coating of cellulose acetate phthalate.

The invention will now be illustrated by the following non-limiting Examples in which, unless stated otherwise:

(i) when given, $^1$H NMR data is quoted and is in the form of delta values for major diagnostic protons, given in parts per million (ppm) relative to tetramethylsilane (TMS) as an internal standard, determined at 300 MHz or 400 MHz using perdeuterio DMSO-D6 (CD$_3$SOCD$_3$), methanol-D4 (CD$_3$OD) or CDCl$_3$ as the solvent unless otherwise stated;

(ii) mass spectra (MS) were run with an electron energy of 70 electron volts in the chemical ionisation (CI) mode using a direct exposure probe; where indicated ionisation was effected by electron impact (EI) or fast atom bombardment (FAB) or electrospray (ESI); where values for m/z are given, generally only ions which indicate the parent mass are reported, and unless otherwise stated the mass ion quotedis the positive mass ion—(M+H)$^+$;

(iii) the title and sub-title compounds of the examples and methods were named using the ACD/Index name program version 4.55 from Advanced Chemistry Development, Inc;

(iv) unless stated otherwise, reverse phase HPLC was conducted using a Symmetry, NovaPak or Xterra reverse phase silica column; and (v) the following abbreviations are used:

| RPHPLC | reverse phase HPLC |
|---|---|
| DMAP | dimethylaminopyridine |
| EDCI | Ethyl dimethylaminopropyl carbodiimide |
| aq | aqueous |
| HOBT | 1-hydroxybenzotriazole |

Intermediate Preparation A

This illustrates the preparation of (R) α-(aminomethyl)-4-(3,4-dichlorophenoxy)-1-piperidineethanol a) (S) 2-[3-[4-(3,4-Dichlorophenoxy)-1-piperidinyl]-2-hydroxypropyl]-1H-isoindole-1,3(2H)-dione (R) 2-(Oxiranylmethyl)-1H-isoindole-1,3(2H)-dione (Tetrahedron Asymmetry, 1996, 7, 1641, 5 g) in a mixture of 50 ml of ethanol and 15 ml of DMF was treated with 4-(3,4-dichlorophenoxy)-piperidine (6 g). The mixture was stirred overnight at room temperature. The solution was concentrated under vacuum and the residue was azeotroped twice with toluene. The crude material was purified by chromatography (ethyl acetate) to give the subtitle compound as a yellow oil.

MS (APCI) 449/451 (MH$^+$)

$^1$H NMR (CDCl$_3$) 7.92-7.81 (2H, m); 7.77-7.70 (2H, m); 7.30 (1H, d); 6.98 (1H, t); 6.74 (1H, dt); 4.34-4.20 (1H, m); 4.09-3.97 (1H, m); 3.83 (1H, dd); 3.73 (1H, dd); 2.93-2.79 (1H, m); 2.73-2.60 (1H, m); 2.59-2.37 (3H, m); 2.31 (1H, t); 2.02-1.86(2H, m); 1.86-1.67 (2H, m).

b) (R) α-(Aminomethyl)$_4$-(3,4-dichlorophenoxy)-1-piperidineethanol (S) 2-[3-[4-(3,4-Dichlorophenoxy)-1-piperidinyl]-2-hydroxypropyl]-1H-isoindole-1,3(2H)-dione (4 g) in ethanol (100 ml) was treated with 20 ml of hydrazine monohydrate and the resulting mixture was refluxed for 3 hours. The reaction was cooled and filtered. The filtrate was evaporated and the product was chromatographed (ethyl acetate) to give the title compound as a yellow oil which solidified on standing (2.5 g).

MS (APCI) 319/321 (MH$^+$)

$^1$H NMR (CDCl$_3$) 7.31 (1H, d); 7.00 (1H, d); 6.75 (1H, dd); 4.0 (1H, app. Sept.); 3.74-3.62 (1H, m); 2.94-2.84 (1H, m); 2.82 (1H, d); 2.72-2.61 (1H, m); 2.65 (1H, d); 2.60-2.49 (1H, m); 2.46-2.21 (3H, m); 2.06-1.901 (2H, m); 1.90-1.72 (2H, m).

Intermediate Preparation B

4-(3,4-dichlorophenoxy)-1-piperidinebutanoic acid hydrochloride a) methyl 4-(3,4-dichlorophenoxy)-1-piperidinebutanoate 4-(3,4-Dichlorophenoxy)piperidine (4.15 g) was dissolved in acetone (80 ml). Potassium carbonate (2.42 g), sodium iodide (0.49 g) and then methyl 4-bromobutyrate (1.95 ml) were added and the mixture was stirred for 42 h. The solvent was evaporated and the residue was partitioned between water and ethyl acetate. The aqueous phase was extracted with ethyl acetate. The organic phases were dried (MgSO$_4$), filtered and evaporated and the residue was chromatographed eluting with ethyl acetate: triethylamine (99:1) to give the subtitle compound (4.52 g).

MS [M+H]$^+$ (ES+) 346/348

$^1$H NMR (399.978 MHz) δ (CDCl$_3$) 1.73-1.82 (2H, m), 1.82 (2H, quintet), 1.92-2.00 (2H, m), 2.24-2.31 (2H, m), 2.35 (2H, t), 2.37 (2H, t), 2:67-2.74 (2H, m), 3.68 (3H, s), 4.21-4.29 (1H, m), 6.75 (1H, dd), 6.99 (1H, d), 7.30 (1H, d).

b) 4-(3,4-Dichlorophenoxy)-1-piperidinebutanoic acid hydrochloride

Methyl 4-(3,4-dichlorophenoxy)-1-piperidinebutanoate (0.48 g) was dissolved in HCl solution (6M, 10 mL) and methanol (1 mL) was added. The reaction mixture was heated under reflux for 8 days. The solvents were evaporated to give the title compound (0.46 g).

MS [M+H]$^+$ (ES+) 332/334

An analytical sample was purified by HPLC (gradient ammonium acetate/acetonitrile 75% to 5% ;Xterra column) to give 4-(3,4-Dichlorophenoxy)-1-piperidinebutanoic acid:

$^1$H NMR (399.978 MHz) δ (CDCl$_3$) 1.87 (2H, quintet), 1.95-2.06 (2H, m), 2.08-218 (2H, m), 2.62 (2H, dt), 2.76 (2H, t), 2.89 (4H, s), 4.45-4.55 (1H, m), 6.76 (1H, dd, 7.01 (1H, d), 7.34 (1H, d).

Intermediate Preparation C

4-(3-Chloro-4-fluoro-phenoxy)-piperidine

DEAD (0.43 ml) was added to a solution of triphenylphosphine (0.72 g), 3-chloro4-fluorophenol (0.403 g) and 4-hydroxy-piperidine-1-carboxylic acid tert-butyl ester (0.5 g) in THP at room temperature (RT). The resulting mixture was stirred overnight, HCl in dioxan (2 ml of 4M) was added and the mixture stirred at RT overnight. The mrixture was then evaporated to dryness and triethylamine (5 ml) was added. The mixture was evaporated and the residue was dissolved in methanol (10 ml), placed onto a SCX cartridge (Varian, 10 g, SCX cartridge available from International Sorbent Technology Isolute® Flash SCX-2) and eluted: first with methanol then with 10% NH$_3$ in methanol. The basic fractions were combined and evaporated to give the product as an oil (0.6 g).

$^1$H NMR (299.946 MHz, DMSO-D6) 67 1.34-1.46 (2H, m), 1.83-1.91 (2H, m), 2.53-2.59 (2H, m), 2.87-2.96 (2H, m), 3.22-3.39 (1H, m), 4.39 (1H, septet), 6.92-6.98 (1H, m), 7.17-7.20 (1H, m), 7.30 (1H, t).

The following intermediates were prepared in similar manner to this preparative method:

| | MS: (M + H) |
|---|---|
| 4-(4-chloro-2-methyl-phenoxy)-piperidine | 226/228 |
| 4-(4-chloro-3-fluoro-phenoxy)-piperidine | 230/232 |
| 4-(4-chloro-2-methoxy-phenoxy)-piperidine | 242/244 |
| 4-(4-fluoro-2-methoxy-phenoxy)-piperidine | 226 |
| 4-(4-methoxy-phenoxy)-piperidine | 208 |
| 4-p-tolyloxy-piperidine | 192 |
| 4-(4-chloro-3-methyl-phenoxy)-piperidine | 226/228 |
| 4-(4-chloro-phenoxy)-piperidine | 212/214 |
| 4-(4-fluoro-phenoxy)-piperidine | 196 |
| 4-(2,4-dichloro-phenoxy)-piperidine | 246/248 |
| 4-(2-chloro-4-fluoro-phenoxy)-piperidine | 230/232 |
| 4-(2,4-difluoro-phenoxy)-piperidine | 214 |
| 4-(4-chloro-2-fluoro-phenoxy)-piperidine | 230/232 |
| 4-(4-fluoro-2-methyl-phenoxy)-piperidine | 210 |
| 4-(4-chloro-2,6-dimethyl-phenoxy)-piperidine | 240/242 |
| 4-(2,3-dichloro-phenoxy)-piperidine | 246/248 |
| 4-(2,5-dichloro-phenoxy)-piperidine | 246/248 |
| 4-(2-chloro-4-methyl-phenoxy)-piperidine | 226/228 |
| 4-(2-chloro-5-methyl-phenoxy)-piperidine | 226/228 |
| 4-(2-chloro-6-methyl-phenoxy)-piperidine | 226/228 |
| 4-(4-chloro-2-ethyl-phenoxy)-piperidine | 240/242 |
| 7-(piperidin-4-yloxy)-quinoline | 229 |
| 4-(2-tert-butyl-phenoxy)-piperidine | 234 |
| 4-(indan-5-yloxy)-piperidine | 218 |
| 4-(4-chloro-2-cyclohexyl-phenoxy)-piperidine | 294/296 |
| 5-chloro-2-(piperidin-4-yloxy)-benzamide | 255/257 |
| 4-(4-chloro-2-isoxazol-5-yl-phenoxy)-piperidine | 279/281 |
| 4-(5-chloro-2-methyl-phenoxy)-piperidine | 226/228 |
| 4-phenoxy-piperidine | 178 |
| 4-(2,4-dichloro-6-methyl-phenoxy)-piperidine | 260/262 |
| 4-(3-chloro-4-methyl-phenoxy)-piperidine | 226/228 |
| 5-chloro-2-(piperidin-4-yloxy)-benzonitrile | 237/239 |

-continued

| | MS: (M + H) |
|---|---|
| 4-(2,4-dichloro-3-methyl-phenoxy)-piperidine | 260/262 |
| 4-(2-ethyl-4-fluoro-phenoxy)-piperidine | 224 |
| 4-(4-methanesulfonyl-phenoxy)-piperidine | 297 |
| 4-(3,4-dichloro-2-methylphenoxy)-piperidine | 260/262 |

Intermediate Preparation D

3-[4-(3,4-Dichlorophenoxy)-1-piperidinyl]propylamine

Step a: 1,1-dimethylethyl [3-[4-(3,4-dichlorophenoxy)-1-piperidinyl]propyl]-carbamate 4-(3,4-Dichlorophenoxy)piperidine (10 g) was dissolved in N,N-dimethylformamide (DMF; 50 ml) and triethylamine (14.8 ml) was added. 1,1-Dimethylethyl (3-bromopropyl)-carbamate (10 g) was added and the solution was stirred at room temperature for 24 hrs. The solvent was evaporated and the resulting solid was dissolved in ethyl acetate and water was added, the organic phase was separated, dried with MgSO$_4$ and evaporated to give the subtitle compound as a solid (17.51 g).

M$^+$: ESI (+ve): 403/405 (M+H)

Step b: 4-(3,4-dichlorophenoxy)-1-piperidinepropanamine

The product from Step (a) (2 g) was dissolved in dioxane (100 ml) and 6N HCl (100 ml) was added. After 18 hours at room temperature the solvent was evaporated and the resultant solid was dissolved in aqueous NaOH (2M) to pH 11. The solution was extracted with ethyl acetate, the organic phase was dried (MgSO$_4$) and evaporated to leave the title compound as an oil (1.1 g).

M$^{3o}$: ESI (+ve): 303/305 (M+H)

Intermediate Preparation E

4(3,4-Dichlorophenoxy)-1-piperidineethanamine

Step a: 1,1-dimethylethyl [2-[4-(3,4dichlorophenoxy)-1-piperidinyl]ethyl]-carbamate 4-(3,4-Dichlorophenoxy)piperidine (8.6 g) was dissolved in DMF (60 ml) and triethylamine (12 ml) was added. 1,1-Dimethylethyl (2-bromoethyl)-carbamate (7.8 g) was added and the solution was stirred at room temperature for 12 hours. Diethyl ether/water (1:1500 ml) was added and the organic phase was separated, dried (MgSO$_4$) and evaporated. Purification by chromatography (dichloromethane: methanol: NH$_3$ (aq) 98.5:1:0.5) gave the subtitle compound (10 g).

MS: APCI (+ve): 389/391(M+H)

Step b: 4-(3,4-dichlorophenoxy)-1-piperidineethanamine

The product from Step a (10 g) was dissolved in dichloromethane (200 ml) and trifluoroacetic acid (100 ml) was added. After 12 hours at room temperature the solvent was evaporated and the resultant solid was washed with diethyl ether and filtered. The solid was dissolved in H$_2$O, made alkaline with NaOH (2N) to pH 11. The solution was extracted with dichloromethane, the organic phase was dried (MgSO$_4$), filtered and evaporated to give the subtitle compound (3.5 g).

MS: APCI (+ve): 289/291 (M+H)

Intermediate Preparation F 4-(3,4-dichlorophenoxy)-1-piperidineethanesulfonamide a) 4-(3,4-dichlorophenoxy)-1-piperidineethanesulfonic acid, sodium salt Vinylsulfonic acid sodium salt (3.3 mL of 30% solution in H$_2$O) was added to 4-(3,4-dichlorophenoxy)-piperidine (2.46 g) and the resulting mixture was heated overnight at reflux. The solvents were evaporated to give the subtitle compound (3.5 g).

MS [M+H]$^+$ (ES+) 354/356 b) 4-(3,4-dichlorophenoxy)-1-piperidineethanesulfonyl chloride 4-(3,4-dichlorophenoxy)-1-piperidineethanesulfonic acid, sodium salt (3.5 g) was dissolved in dichloromethane (5 mL). Thionyl chloride (5 mL) was added and the reaction mixture was heated under reflux for 72 h. The solvents were evaporated to give the subtitle compound (4.2 g)

A small aliquot was dissolved in methanol and gave methyl-4-(3,4-dichlorophenoxy)-1-piperidineethanesulfonate.

MS [M+H]$^+$ (ES+) 368/370 c) 4-(3,4-dichlorophenoxy)-1-piperidineethanesulfonamide

Ammonia in 1,4-dioxane (5 mL of 0.5M) was added to 4-(3,4-dichlorophenoxy)-1-piperidineethanesulfonyl chloride (2 g) and the mixture was stirred at room temperature for 2 h. The solvents were evaporated and the residue was chromatographed eluting with dichloromethane: methanol: ammonia (94:5:1) to give the title compound (0.14 g).

MS [M+H]$^+$(ES+) 353/355

Intermediate Preparation G 4-methyl-N-(1-oxo-2-propenyl)-benzenesulfonamide

Acryloyl chloride (0.26 mL) and p-toluenesulfonanide (0.50 g) were dissolved in dichloromethane (5 mL) and triethyamine (0.46 mL) was added. The reaction mixture was stirred for 3 h and NaOH solution (2M, 5 mL) was added. The organic layer was separated, the aqueous layer was acidified with HCl (2M) and extracted with dichloromethane. The organic layers were combined, dried over MgSO$_4$ and evaporated to give the subtitle compound (0.14 g)

MS [M+H]$^+$ (ES+) 225

EXAMPLE 1

This Example illustrates the preparation of N-[[[2-[4-(3,4-dichlorophenoxy)-1-piperidinyl]ethyl]amino]carbonyl]-4-methyl-benzenesulfonamide, which conforms to formula (Ia).

To a solution of 4-(3,4-dichlorophenoxy)-1-piperidineethanamine (WO00/58305) (0.134 g) in dichloromethane was added 4-methyl-benzenesulfonyl isocyanate (0.092 g) dropwise and the reaction was stirred under nitrogen for 2 hours. The solvent was removed under reduced pressure and the resulting product was purified by RPHPLC (XTerra Waters column; gradient, 90% 0.2% aq ammonia/acetonitrile decreasing to 5% over 10 mins). Recrystallisation of the product from ethanol/dichloromethane, gave the title compound (0.046g; MS [M+H]$^+$ (ES+) 486/488; m.pt. 179.6-180.3° C.).

$^1$H NMR (399.98 MHz, CD$_3$OD) δ 1.68-1.78 (m, 2H), 1.93-2.00 (m, 2H), 2.32-2.39 (m, 2H), 2.35 (s, 3H), 2.41-2.46 (m, 2H), 2.67-2.75 (m, 2H), 3.17-3.22 (m, 2H), 4.34-

4.40 (m, 1H), 6.86-6.89 (m, 1H), 7.06-7.08 (m, 1H), 7.21-7.25 (m, 2), 7.36-7.39 (m, 1H), 7.75-7.78 (m, 2H); plus 1 drop of 30% NaOD in $D_2O$.

The compounds of Examples 2-16 (see table below; all compounds of formula (Ia)) were prepared following the method of Example 1 using the appropriate amine and sulfonylisocyanate.

EXAMPLE 17

N-[[[2-[4-(3,4-dichlorophenoxy)-1-piperidinyl]ethyl] aamino]carbonyl]-3-(trifluoromethy)-benzenesulfonamide (an example of a compound of formula (Ia))

p-Nitrophenylchloroformate (0.11 g) was dissolved in dichloromethane (5 ml). DMAP (67 mg) was added followed after 2 min by 3-trifluoromethylbenzenesulfonamide (0.13 g). Triethylamine (0.10 ml) was added followed by a solution of 4-(3,4-dichlorophenoxy)-1-piperidineethanamine (0.15 g) in dichloromethane (1 ml). The resulting solution was stirred for 40 h. The solvents were evaporated and the residue was purified by HPLC (Waters XTerra® column, 0.2% aq ammonia: acetonitrile gradient 75%-25% aq) to give the title compound (93 mg).

m. pt. 194-201° C.
MS [M+H]$^+$ (ES+) 540/542
$^1$H NMR δ (DMSO) 1.64-1.82 (2H, m), 1.92-2.05 (2H, m), 2.56-270 (5H, m), 3.15 (2H, t), 4.45-4.54 (1H, m), 6.97 (1H, dd), 7.22 (1H, d), 7.47 (1H, d), 7.75 (1H, t), 7.90 (1H, d).

EXAMPLE 18

N-benzoyl-N'-[3-[4-(3,4-dichlorophenoxy)-1-piperidinyl]propyl]-sulfamide (an example of a compound of formula (Ib))

4-(3,4-Dichlorophenoxy)-1-piperidineethanamine (0.16 g) was dissolved in dichloromethane (2 ml) and triethylamine (88 µl) was added. Benzoylsulfamoyl chloride (0.13 g) was added and the solution was stirred for 16 h. The solvent was evaporated and the residue was purified by HPLC (ammonium acetate: acetonitrile 95% to 5% aq) to give the title compound (6 mg).

m. pt. 93-106° C.
MS [M+H]$^+$ (ES+) 486/490
$^1$H NMR δ ($CD_3OD$) 1.95 (2H, quintet), 2.00-2.11 (2H, m), 2.17-2.28 (2H, m), 3.16 (2H, t), 3.16-3.22 (2H, m), 4.54-4.60 (1H, m), 4.63-4.68 (1H, m), 6.95 (1H, dd), 7.20 (1H, d), 7.34-7.50 (4H, m), 7.98-8.02 (2H, m).

EXAMPLE 19

N-(2-Chlorobenzoyl)-4-(3,4-dichlorophenoxy)-1-piperidineethanesulfonamide (an example of a compound of formula (Id))

4-(3,4-Dichlorophenoxy)-1-piperidineethanesulfonamide (0.1 g), EDCI (0.108 g), HOBT (40 mg), DMAP (40 mg) and 2-chlorobenzoic acid (88 mg) were dissolved in dichloromethane (5 mL) and triethylamine (0.5 mL) was added. The reaction mixture was stirred for 17 h. The solvents were evaporated. The residue was purified by HPLC (gradient Ammonium acetate/Acetonitrile 95% to 25%; Xterra column) to give the subtitle compound (40 mg)

m. pt. 237-239° C.
MS [M+H]$^+$ (ES+) 492/494/496
$^1$H NMR (399.98 MHz) δ ($CD_3OD$) 1.73-1.84 (2H, m), 2.02 (2H, dt), 2.48 (2H, t), 2.81 (2H, t), 2.96 (2H, dd), 3.55 (2H, dd), 4.43 (1H, t), 6.90 (1H, dd), 7.10 (1H, d), 7.25-7.33 (2H, m), 7.35-7.39 (2H, m), 7.48-7.53 (1H, m).

EXAMPLE 20

N-[3-[4-(3,4-dichlorophenoxy)-1-piperidinyl]-1-oxopropyl]4-methyl-benzenesulfonamide (an example of a compound of formula (Ic))

4-Methyl-N-(1-oxo-2-propenyl)-benzenesulfonamide (0.140 g) was dissolved in THF (10 mL) and 4-(3,4-dichlorophenoxy)-piperidine (0.120 g) and NaOH (0.080 g) were added. The reaction mixture was stirred for 72 h. The solvents were evaporated. The residue was purified by HPLC (gradient Ammonium acetate/Acetonitrile 95% to 5%; Xterra column) to give the title compound (40 mg)

m. pt. 177-179° C.
MS [M+H]$^+$ (ES+) 471/473
$^1$H NMR δ ($CD_3OD$) 1.97-2.09 (2H, m), 2.09-2.21 (2H, m), 2.38 (3H, s), 2.54 (2H, t), 3.15-3.29 (6H, m), 4.64-4.71 (1H, m), 6.98 (1H, dd), 7.23 (1H, d), 7.28 (2H, dd), 7.44 (1H, d), 7.82 (2H, dd).

EXAMPLE 21

N-[4-[4-(3,4-Dichlorophenoxy)-1-piperidinyl]-1-oxobutyl]-4-methyl-benzenesulfonamide (an example of a compound of formula (Ic))

4-(3,4-Dichlorophenoxy)-1-piperidinebutanoic acid hydrochloride (0.250 g) was dissolved in dichloromethane (10 mL) containing p-toluenesulfonamide (0.142 g), dimethylaminopyridine (92 mg) and EDCI (0.158 g) were added. The solution was stirred at room temperature for 4 days. The solvent was evaporated. The crude product was dried in vacuo and then purified by HPLC (at column dilution, gradient ammonium acetate/acetonitrile 75% to 5% ;Waters Xterra® column) and to give the title compound (42 mg).

MS [M+H]$^+$ (ES+) 485/487
$^1$H NMR (299.946 MHz) δ (DMSO) 1.71 (2H, quintet), 1.79-1.93 (2H, m), 2.05-2.17 (2H, m), 2.06-2.35 (2H, m), 2.35 (3H, s), 2.79 (2H, t), 2.82-2.92 (2H, m), 3.00-3.09 (2H, m), 4.58-4.67 (1H, m), 7.04 (1H, dd), 7.29 (2H, d), 7.33 (1H, d), 7.53 (1H, d), 7.72 (2H, d).

The compounds of Examples 22-34 (see table below; all compounds of formula (Ic)) were prepared following the method of Example 21 using the appropriate sulfonamides.

| Example (purification) | Compound | MS [M + H]$^+$ (ES+) | $^1$H NMR | m. pt. (° C.) |
| --- | --- | --- | --- | --- |
| 2 recrystallised from DMSO | N-[[[3-[4-(3,4-dichlorophenoxy)-1-piperidinyl]propyl]amino]carbonyl]-4-methyl-benzenesulfonamide | 500/502 | ($CD_3OD$)1.58-1.67(m, 2H), 1.71-1.80(m, 2H), 1.93-2.01(m, 2H), 2.28-2.37(m, 4H), 2.35(s, 3H), 2.63-2.71(m, 2H), 3.04-3.10(m, 2H),4.36-4.42(m, 1H), | 200 |

-continued

| Example (purification) | Compound | MS [M + H]+ (ES+) | 1H NMR | m. pt. (° C.) |
|---|---|---|---|---|
| | | | 6.86-6.90(m, 1H), 7.07-7.09(m, 1H), 7.21-7.25(m, 2H), 7.38(d, 1H), 7.75-7.78(m, 2H); plus 1 drop of NaOD(30%) in D2O | |
| 3 HPLC in aqueous ammonium acetate - acetonitrile | (R) N-[[[3-[4-(3,4-dichlorophenoxy)-1-piperidinyl]-2-hydroxypropyl]amino]carbonyl]-4-methyl-benzenesulfonamide | 516/518 | (DMSO)1.54-1.66(2H, m), 1.84-1.93(2H, m), 2.21-2.28(2H, m), 2.28-2.32(1H, m), 2.35(3H, s), 2.62-2.73(2H, m), 2.85-2.93(1H, m), 3.07(1H, dt), 3.53-3.59(1H, m), 4.39-4.47(1H, m), 4.81-4.97(1H, m), 6.26-6.35(1H, m), 6.98(1H, dd),7.26(1H, d), 7.31(2H, d), 7.50(1H, d), 7.71(2H, d) | 103.5-106 |
| 4 HPLC in aqueous TFA - methanol | N[[[2-4-(3,4-Dichlorophenoxy)-1-piperidinyl]ethyl]amino]carbonyl]-4-chloro-benzenesulfonamide trifluoroacetate salt | 508/510 | (CDCl3)2.02-2.15(2H, m), 2.17-2.35(2H, m), 2.99-3.22(4H, m), 3.27-3.45(2H, m), 3.50-3.67(2H, m), 4.52-4.63(1H, m), 6.71-6.78(1H, m), 6.97-7.02(1H, m), 7.35(1H, d), 7.42-7.48(2H, m), 7.78-7.89(1H, m), 7.89-7.99(2H, m) | 106-108 |
| 5 | N-[[2-4-(3,4-dichlorophenoxy)-1-piperidinyl]ethyl]amino]carbonyl]-2-methyl-benzenesulfonamide | 486/488 | (DMSO)1.49-1.69(2H, m), 1.79-1.99(2H, m), 2.25-2.41(6H, m), 2.68(3H, bs), 3.07(3H, s), 4.39-4.51(1H, m), 6.35-6.45(1H, m), 7.00(1H, d), 7.21-7.42(3H, m), 7.51(2H, d), 7.88(1H, s) | 178-179 |
| 6 | 4-chloro-N-[[[2-4-(3,4-difluorophenoxy)-1-piperidinyl]ethyl]amino]carbonyl]-benzenesulfonamide | 474/476 | (DMSO)1.53-1.68(2H, m), 1.80-1.98(2H, m), 1.94-2.10(1H, m), 2.71-2.88(1H, m), 3.02-3.16(3H, m), 3.22-3.43(4H, m), 6.76-6.88(1H, m), 7.05-7.20(1H, m), 7.34(1H, dd), 7.46-7.62(2H, m), 7.83(1H, s) | 206-207 |
| 7 | N-[[[2-4-(3,4-difluorophenoxy)-1-piperidinyl]ethyl]amino]carbonyl]-benzenesulfonamide | 440 | (DMSO)1.51-1.69(2H, m), 1.82-2.01 (2H, m), 2.20-2.43(4H, m), 2.64-2.81(2H, m), 3.00-3.18(2H, m), 4.31-4.48(1H, m), 6.40-6.54(1H, m), 6.72-6.88(1H, m), 7.03-7.17(1H, m), 7.32(1H, q), 7.38-7.69(3H, m), 7.87(2H, d) | 187-188 |
| 8 | N-[[[2-4-(2,4-dichloro-3-methylphenoxy)-1-piperidinyl]ethyl]amino]carbonyl]-4-methyl-benzenesulfonamide | 500/502 | (DMSO)1.59-1.71(2H, m), 1.82-1.93(2H, m), 2.27-2.35(4H, m), 2.37(3H, s), 2.40(3H, s), 2.60-2.72(2H, m), 3.00-3.13(2H, m), 4.45-4.55(1H, m), 6.45 (1H, s), 7.11(1H, d), 7.37(3H, t), 7.76(2H, d) | 203-205 |
| 9 | N-[[[2-4-(2-chloro-4-fluorophenoxy)-1-piperidinyl]ethyl]amino]carbonyl]-4-methyl-benzenesulfonamide | 470/472 | (DMSO)1.57-1.69(2H, m), 1.84-1.92(2H, m), 2.21-2.36(3H, m), 2.37(3H, s), 2.58-2.75(3H, m), 3.00-3.12(2H, m), 4.38-4.46(1H, m), 6.44(1H, s), 7.15(1H, td), 7.19-7.31(1H, m), 7.31-7.47(3H, m), 7.76(2H, d) | 150-152 |
| 10 | 4-chloro-N-[[[2-[4-(2,4-dichloro-3-methylphenoxy)-1-piperidinyl]ethyl]amino]carbonyl]-benzenesulfonamide | 520/522/524 | (DMSO)1.63-1.76(2H, m), 1.80-1.99(2H, m), 2.04-2.35(2H, m), 2.41(3H, s), 2.67-2.86(2H, m), 3.10(2H, s), 6.44(1H, s), 7,13(1H, s), 7.37(1H, d), 7.47-7.65(2H, m), 7.84(2H, d)s | 209-210 |
| 11 | N-[[[2-4-(2,4-dichloro-3-methylphenoxy)-1-piperidinyl]ethyl]amino]carbonyl]-2-methyl-benzenesulfonamide | 500/502 | (DMSO)1.17-1.34(1H, m), 1.60-1.73(2H, m), 1.81-1.93(2H, m), 2.40(3H, s), 2.58(3H, s), 2.64-2.76(3H, m), 3.03-3.14(3H, m), 4.51(1H, s), 6.41(1H, s), 7.04-7.16(1H, m), 7.31-7.40(3H, m), 7.52(1H, s), 7.89(1H, d) | 119-120 |
| 12 | N-[[[2-4-(3,4-dichlorophenoxy)-1-piperidinyl]ethyl]amino]carbonyl]-benzenesulfonamide | 472/474 | (DMSO)1.01-1.31(2H, m), 1.48-1.66(1H, m), 1.76-2.02(2H, m), 2.26-2.41(2H, m), 2.67(2H, quintet), 3.03-3.09(2H, m), 7.00(1H, s), 7.27(1H, s), 7.46-7.66(4H, m), 7.84(2H, s) | 183-184 |
| 13 | 2-chloro-N-[[[2-4-(3,4-difluorophenoxy)-1-piperidinyl]ethyl]amino]carbonyl]-benzenesulfonamide | 474/476 | (DMSO)1.50-1.75(2H, m), 1.79-2.12(2H, m), 2.22-2.40(2H, m), 2.73-2.88(3H, m), 3.00-3.19(4H, m), 4.34-4.74(1H, m), 6.27-6.39(1H, m), 6.71-6.94(1H, m), 7.08-7.23(1H, m), 7.29-7.59(4H, m), 7.84(2H, s) | 160-161 |
| 14 Starting amine described in EP0903349 | N-[[[(1S)-1-[[4-[(3,4-dichlorophenyl)methyl]-1-piperidinyl]methyl]-2-methylpropyl]amino]carbonyl]-4-methyl-benzenesulfonamide | 526/528 | (DMSO)0.80(6H, d), 1.19(2H, d), 1.46(3H, s), 1.66-1.76(1H, m), 1.83-1.94(2H, m), 2.20-2.38(5H, m), 2.49(2H, d), 2.79(2H, d), 3.67(1H, s), 7.08(1H, dd), 7.18(2H, d), 7.30(1H, d), 7.41(1H, d), 7.75(2H, d) | 120-126 |
| 15 | 4-chloro-N-[[[(1S)-1-[[4-[(3,4-dichlorophenyl)methyl]-1-piperidinyl]methyl]-2-methylpropyl]amino]carbonyl]-benzenesulfonamide | 547/549/551 | (CD3OD)0.77-0.84(6H, m), 1.18(2H, t), 1.40-1.55(3H, m), 1.71(1H, dd), 1.81-1.96(2H, m), 2.21-2.37(2H, m), 2.49(2H, d), 2.79(2H, t), 3.66(1H, s), 7.08(1H, dd), 7.31(1H, d), 7.39(3H, dd), 7.85(2H, d) | 182-188 |
| 16 | N-[[[2-4-[(3,4-dichlorophenyl)methyl]-1-piperidinyl]ethyl]amino]carbonyl]-4-methyl-benzenesulfonamide | 484/486 | (CD3OD)1.19-1.32(2H, m), 1.45-1.59(3H, m), 1.93(2H, t), 2.35(3H, s), 2.37(2H, t), 2.51(2H, d), 2.86(2H, m), 3.13-3.20(2H, m), 7.08(1H, dd), 7.22(2H, d), 7.30(1H, d), 7.39(1H, d), 7.75(2H, dd) | |
| 22 | 4-chloro-N-[4-[4-(3,4-dichlorophenoxy)-1-piperidinyl]-1-oxobutyl]-benzenesulfonamide | 506/508/510 | (CD3OD)1.66-1.80(4H, m), 1.91-2.02(2H, m), 2.13(2H, t), 2.21-2.36(4H, m), 2.68(2H, s), 4.37(1H, dt), 6.88(1H, dd), 7.08(1H, d), 7.37(1H, d), 7.45 (2H, d), 7.88(2H, dt) | 208-211 |
| 23 | 3,5-dichloro-N-[4-[4-(3,4-dichlorophenoxy)-1-piperidinyl]-1-oxobutyl]-benzenesulfonamide | 539/541/543 | | |
| 24 | N-[4-[4-(3,4-dichlorophenoxy)-1-piperidinyl]-1-oxobutyl]-3-(trifluoromethyl)-benzenesulfonamide | 539/541 | | |

-continued

| Example (purification) | Compound | MS [M + H]+ (ES+) | $^1$H NMR | m. pt. (° C.) |
|---|---|---|---|---|
| 25 | methyl 2-[[[4-[4-(3,4-dichlorophenoxy)-1-piperidinyl]-1-oxobutyl]amino]sulfonyl]-benzoate | 529/531 | | |
| 26 | 5-chloro-N-[4-[4-(3,4-dichlorophenoxy)-1-piperidinyl]-1-oxobutyl]-2-thiophenesulfonamide | 511/513/515 | | |
| 27 | 5-bromo-N-[4-[4-(3,4-dichlorophenoxy)-1-piperidinyl]-1-oxobutyl]-2-thiophenesulfonamide | 555/557/559 | | |
| 28 | 4,5-dichloro-N-[4-[4-(3,4-dichlorophenoxy)-1-piperidinyl]-1-oxobutyl]-2-thiophenesulfonamide | 545/547/549 | | |
| 29 | 2,5-dichloro-N-[4-[4-(3,4-dichlorophenoxy)-1-piperidinyl]-1-oxobutyl]-3-thiophenesulfonamide | 545/547/549 | | |
| 30 | 4-bromo-N-[4-[4-(3,4-dichlorophenoxy)-1-piperidinyl]-1-oxobutyl]-2-thiophenesulfonamide | 555/557/559 | | |
| 31 | 6-bromo-N-[4-[4-(3,4-dichlorophenoxy)-1-piperidinyl]-1-oxobutyl]-3-pyridinesulfonamide | 550/552/554 | | |
| 32 | N-[4-[4-(3,4-dichlorophenoxy)-1-piperidinyl]-1-oxobutyl]-2,5-difluoro-benzenesulfonamide | 507/509 | | |
| 33 | N-[4-[4-(3,4-dichlorophenoxy)-1-piperidinyl]-1-oxobutyl]-2,4,5-trifluoro-benzenesulfonamide | 525/527 | | |
| 34 | 5-chloro-N-[4-[4-(3,4-dichlorophenoxy)-1-piperidinyl]-1-oxobutyl]-2,4-difluoro-benzenesulfonamide | 541/543/545 | | |

EXAMPLE 22

Pharmacological Analysis: Calcium Flux $[Ca^{2+}]_i$ Assay

Human Eosinophils

Human eosinophils were isolated from EDTA anticoagulated peripheral blood as previously described (Hansel et al., *J. Immunol. Methods*, 1991, 145, 105-110). The cells were resuspended ($5 \times 10^6$ ml$^{-1}$) and loaded with 5 μm FLUO-3/AM+Pluronic F127 2.2 μl/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at $2.5 \times 10^6$ ml$^{-1}$. The cells were then transferred to 96 well FLIPr plates (Poly-D-Lysine plates from Becton Dickinson pre-incubated with 5 μM fibronectin for two hours) at 25 μl/well. The plate was centrifuged at 200 g for 5 min and the cells were washed twice with LKS (200 μl; room temperature).

A compound of the Examples was pre-dissolved in DMSO and added to a final concentration of 0.1%(v/v). DMSO. Assays were initiated by the addition of an A$_{50}$ concentration of eotaxin and the transient increase in fluo-3 fluorescence ($1_{Ex}$=490 nm and $1_{Em}$=520 nm) monitored using a FLIPR (Fluorometric Imaging Plate Reader, Molecular Devices, Sunnyvale, U.S.A.).

Human Eosinophil Chemotaxis

Human eosinophils were isolated from EDTA anticoagulated peripheral blood as previously described (Hansel et al., *J. Immunol. Methods*, 1991, 145, 105-110). The cells were resuspended at $10 \times 10^6$ ml$^{-1}$ in RPMI containing 200 IU/ml penicillin, 200 μg/ml streptomycin sulfate and supplemented with 10% HIFCS, at room temperature.

Eosinophils (700 μl) were pre-incubated for 15 mins at 37° C. with 7 μl of either vehicle or compound (100× required final concentration in 10% DMSO). The chemotaxis plate (ChemoTx, 3μ, pore, Neuroprobe) was loaded by adding 28 μl of a concentration of eotaxin (0.1 to 100 nM) containing a concentration of a compound according to the Examples or solvent to the lower wells of the chemotaxis plate. The filter was then placed over the wells and 25 μl of eosinophil suspension were added to the top of the filter. The plate was incubated for 1 hr at 37° C. in a humidified incubator with a 95% air/5% CO$_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 μl of PBS containing 0.5% Triton×100 followed by two cycles of freeze/thawing. The cell lysate was then added to the supernatant. The number of eosinophils migrating was quantified according to the method of Strath et al., *J. Immunol. Methods*, 1985, 83, 209 by measuring eosinophil peroxidase activity in the supernatant.

The compound of Example 1 was found to be an antagonist of the eotaxin mediated human eosinophil chemotaxis.

EXAMPLE 23

Guinea-pig Isolated Trachea (See for example, Harrison, R. W. S., Carswell, H. & Young, J. M. (1984) European J. Pharmacol., 106, 405-409.)

Male albino Dunkin-Hartley guinea-pigs (250 g) were killed by cervical dislocation and the whole trachea removed. After clearing the adherent connective tissue, the trachea was cut into six ring segments each three cartilage bands wide and then suspended in 20 ml organ baths containing Krebs-Henseleit solution of the following composition (MM): NaCl 117.6, $NaH_2PO_4$ 0.9, $NaHCO_3$ 25.0, $MgSO_4$ 1.2, KCl 5.4, $CaCl_2$ 2.6 and glucose 11.1. The buffer was maintained at 37° C. and gassed with 5% $CO_2$ in oxygen. Indomethacin (2.8 μM) was added to the Krebs solution to prevent development of smooth muscle tone due to the synthesis of cyclo-oxygenase products. The tracheal rings were suspended between two parallel tungsten wire hooks, one attached to an Ormed beam isometric force transducer and the other to a stationary support in the organ bath. Changes in isometric force were recorded on 2-channel Sekonic flat bed chart recorders.

Experimental Protocols

At the beginning of each experiment a force of 1 g was applied to the tissues and this was reinstated over a 60 minute equilibration period until a steady resting tone was achieved. Subsequently, a cumulative histamine concentration effect (E/[A]) curve was constructed at 0.5 $log_{10}$ unit increments, in each tissue. The tissues were then washed and approximately 30 minutes later, test compound or vehicle (20% DMSO) was added. Following an incubation period of 60 minutes a second E/[A] curve was performed to histamine.

Contraction responses were recorded as a percentage of the first curve maximum. Data analysis Experimental E/[A] curve data were analysed for the purposes of estimating the potencies ($p[A_{50}]$ values) of histamine in the absence and presence of the test compound. Affinity ($pA_2$) values of test compounds were subsequently calculated using the following equation:

$$\log(r-1) = \log[B] + pA_2$$

where $r = [A]_{50}$ in presence of test compound/$[A]_{50}$ in absence of antagonist and [B] is the concentration of test compound. The compound of Example 1 was found to be an H1 antagonist.

The invention claimed is:

1. A compound of formula (I):

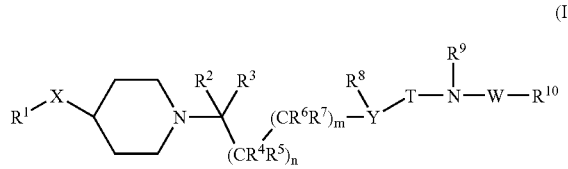

(I)

wherein:
T is C(O) or $S(O)_2$;
W is C(O) or $S(O)_2$;
X is O;
Y is $CR^{11}$ or N;
n is 0, 1 or 2;
m is 1 or, when Y is $CR^{11}$ m is 0;
$R^1$ is optionally substituted aryl or optionally substituted heterocyclyl;
$R^2$, $R^3$, $R^4$, $R^5$, $R^6$, $R^7$ and $R^8$ are, independently, hydrogen or $C_{1-6}$ alkyl; wherein these alkyl groups are optionally substituted by OH, provided that when Y is N then $R^8$ does not have a hydroxy on the carbon atom bonded to Y;
or $R^2$ and $R^3$, $R^4$ and $R^5$, or $R^6$ and $R^7$, together with the atom to which they are attached, form a 3-7 membered carbocyclic ring;
$R^4$ may additionally be OH or $C_{1-6}$ alkoxy;
when Y is $CR^{11}$ the group $R^6$ may additionally be OH or $C_{1-6}$ alkoxy;
provided that only one $R^4$ or $R^6$ is OH;
$R^9$ is hydrogen or $C_{1-6}$ alkyl;
$R^{10}$ is alkyl, optionally substituted aryl, optionally substituted aralkyl or optionally substituted heterocyclyl;
$R^{11}$ is hydrogen or $C_{1-6}$ alkyl;
wherein the foregoing aryl and heterocyclyl moieties are optionally substituted by: halogen, cyano, nitro, hydroxy, oxo, $S(O)_pR^{12}$, $OC(O)NR^{13}R^{14}$, $NR^{15}R^{16}$, $NR^{17}C(O)R^{18}$, $NR^{19}C(O)NR^{20}R^{21}$, $S(O)_2NR^{22}R^{23}$, $NR^{24}S(O)_2R^{25}$, $C(O)NR^{26}R^{27}$, $C(O)R^{28}$, $CO_2R^{29}$, $NR^{30}CO_2R^{31}$, $C_{1-6}$ alkyl, $CF_3$, $C_{1-6}$ alkoxy($C_{1-6}$)alkyl, $C_{1-6}$ alkoxy, $OCF_3$, $C_{1-6}$ alkoxy($C_{1-6}$)alkoxy, $C_{1-6}$ alkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, phenyl, phenyl($C_{1-4}$)alkyl, phenoxy, phenylthio, phenyl($C_{1-4}$)alkoxy, heteroaryl, heteroaryl($C_{1-4}$)alkyl, heteroaryloxy or heteroaryl($C_{1-4}$)alkoxy; wherein any of the immediately foregoing phenyl and heteroaryl moieties are optionally substituted with halogen, hydroxy, nitro, $S(O)_q(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$;
p and q are, independently, 0, 1 or 2;
$R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{26}$, $R^{27}$, $R^{28}$, $R^{29}$ and $R^{30}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2$ $NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);
alternatively $NR^{13}R^{14}$, $NR^{15}R^{16}$, $NR^{20}R^{21}$, $NR^{22}R^{23}$, $NR^{26}R^{27}$, and $N(C_{1-4}$ alkyl)$_2$ may, independently, form a 4-7, membered heterocyclic ring, azetidine, pyrrolidine, piperidine, azepine, 1,4-morpholine or 1,4-piperazine, the latter optionally substituted by $C_{1-4}$alkyl on the distal nitrogen;
$R^{12}$, $R^{25}$ and $R^{31}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^{13}$ and $R^{14}$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^{13}$ and $R^{14}$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^{13}$ and $R^{14}$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^{13}$ and $R^{14}$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^{13}$ and $R^{14}$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^{13}$ and $R^{14}$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);

or an N-oxide thereof; or a pharmaceutically acceptable salt thereof.

2. A compound as claimed in claim 1 wherein $R^1$ is phenyl substituted with one or more of fluorine, chlorine, $C_{1-4}$ alkyl or $C_{1-4}$ alkoxy.

3. A compound as claimed in claim 1 wherein one of T and W is C(O) and the other is $S(O)_2$.

4. A compound as claimed in claim 1 wherein T is C(O).

5. A compound as claimed in claim 1 wherein W is $S(O)_2$.

6. A compound as claimed in claim 1 wherein Y is CH.

7. A compound as claimed in claim 1 wherein m and n are both 1.

8. A compound as claimed in claim 1 wherein $R^2$, $R^3$, $R^4$, $R^5$, $R^6$, $R^7$, $R^8$ and $R^9$ are all hydrogen.

9. A compound as claimed in claim 1 wherein $R^{10}$ is substituted phenyl, the substituents being chosen from those provided in claim 1.

10. A compound as claimed in claim 9 wherein $R^{10}$ is phenyl optionally substituted by: halo, hydroxy, nitro, cyano, amino, $C_{1-4}$ alkyl (itself optionally substituted by $S(O)_2(C_{1-4}$ alkyl), $S(O)_2$phenyl), $C_{1-4}$ alkoxy, $S(O)_kR^{32}$ (wherein k is 0, 1 or 2; and $R^{32}$ is $C_{1-4}$ alkyl, $C_{1-4}$ hydroxyalkyl, $C_{3-7}$ cycloalkyl($C_{1-4}$ alkyl) or phenyl), $C(O)NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl)$_2$ (and these alkyl groups may join to form a ring).

11. A process for preparing a compound of formula (I) as claimed in claim 1, the process comprising:

a. when $R^9$ is hydrogen, T is C(O) and Y is N, reacting a compound of formula (II):

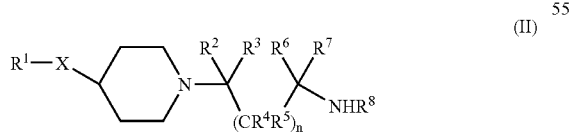

(II)

with an isocyanate of formula $R^{10}WN=C=O$ in the presence of a suitable solvent at a suitable temperature;

b. when $R^9$ is hydrogen, T is C(O) and Y is N, reacting a compound of formula (II) with the adduct formed between p-nitrophenyl chloroformate and an amide $R^{10}WNH_2$, in the presence of dimethylaminopyridine;

c. when $R^9$ is hydrogen, T is $S(O)_2$, W is C(O) and Y is N, reacting a compound of formula (IX):

(IX)

with a compound of formula (II) in the presence of a suitable base in a suitable solvent at a suitable temperature;

d. when T and W are both $S(O)_2$ and Y is N, reacting a compound of formula (X):

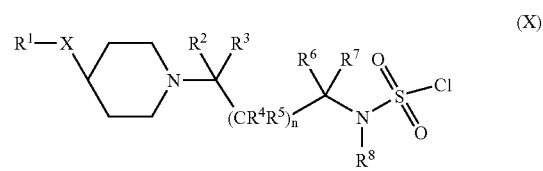

(X)

with a sulfonamide of formula $R^{10}S(O)_2NHR^9$ in the presence of a base in a suitable solvent at a temperature in the range 50-110° C.;

e. when T and W are both $S(O)_2$ and Y is N, reacting a compound of formula (Xa):

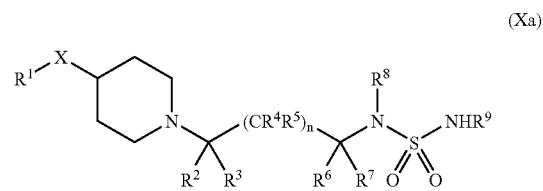

(Xa)

with a sulfonyl chloride of formula $R^{10}SO_2Cl$ in the presence of a base, in a suitable solvent at a temperature in the range 50-110° C.;

f. when T is $S(O)_2$, W is CO and Y is N, reacting a compound of formula (Xa) with an acid $R^{10}COOH$ in the presence of an appropriate coupling agent in a suitable solvent;

g. when $R^2$ is hydrogen, T is C(O), W is $S(O)_2$ and Y is $CR^{11}$, by firstly hydrolysing a compound of formula (XI):

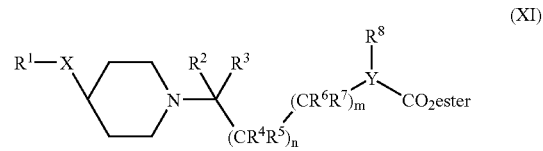

(XI)

wherein suitable ester groups include $C_{1-6}$ alkyl groups, and reacting the product so formed with $R^{10}S(O)_2NHR^9$ in the presence of an appropriate coupling agent in a suitable solvent;

h. when T and W are both C(O) and Y is $CR^{11}$, heating a compound of formula (XIV):

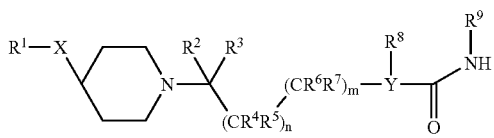
(XIV)
in the presence of $R^{10}C(OR')_2N(CH_3)_2$ or $R^{10}C(OR')_3$, wherein R' is methyl or ethyl, or $(OR')_3$ is $(OCH_2)_3CCH_3$; or,
i. when $R^9$ is alkyl, alkylating a compound of formula (I) where $R^9$ is H with an appropriate alkylating agent $R^9$-L, wherein L is a leaving group in the presence of a suitable base in a suitable solvent.
* * * * *

UNITED STATES PATENT AND TRADEMARK OFFICE
CERTIFICATE OF CORRECTION

PATENT NO. : 7,265,227 B2  Page 1 of 1
APPLICATION NO. : 10/483138
DATED : September 4, 2007
INVENTOR(S) : Richard Evans et al.

It is certified that error appears in the above-identified patent and that said Letters Patent is hereby corrected as shown below:

Column 32
Line 29, delete "C.;" insert -- C; --
Line 44, delete "C.;" insert -- C; --

Column 34
Line 1, delete "$_{or}R^{10}$" insert -- $R^{10}$ --

Signed and Sealed this

Twelfth Day of August, 2008

JON W. DUDAS
*Director of the United States Patent and Trademark Office*